United States Patent
Hemmer et al.

(10) Patent No.: US 9,297,809 B2
(45) Date of Patent: Mar. 29, 2016

(54) MEANS AND METHODS FOR DIAGNOSING AND TREATING MULTIPLE SCLEROSIS

(75) Inventors: Bernhard Hemmer, München (DE); Rajneesh Srivastava, München (DE)

(73) Assignee: KLINIKUM RECHTS DER ISAR DER TECHNISCHEN UNIVERSITÄT MÜNCHEN, München (DE)

( * ) Notice: Subject to any disclaimer, the term of this patent is extended or adjusted under 35 U.S.C. 154(b) by 149 days.

(21) Appl. No.: 14/122,318

(22) PCT Filed: May 23, 2012

(86) PCT No.: PCT/EP2012/059622
§ 371 (c)(1),
(2), (4) Date: Nov. 26, 2013

(87) PCT Pub. No.: WO2012/163765
PCT Pub. Date: Dec. 6, 2012

(65) Prior Publication Data
US 2014/0080156 A1    Mar. 20, 2014

(30) Foreign Application Priority Data
May 30, 2011    (EP) .................................... 11004423

(51) Int. Cl.
| G01N 33/53 | (2006.01) |
| G01N 33/68 | (2006.01) |
| C07K 16/28 | (2006.01) |
| C07K 14/705 | (2006.01) |

(52) U.S. Cl.
CPC .......... *G01N 33/6854* (2013.01); *C07K 14/705* (2013.01); *C07K 16/28* (2013.01); *C07K 2317/21* (2013.01); *C07K 2317/70* (2013.01); *C07K 2317/734* (2013.01); *C07K 2319/21* (2013.01); *C07K 2319/22* (2013.01)

(58) Field of Classification Search
None
See application file for complete search history.

(56) References Cited

U.S. PATENT DOCUMENTS

| 2011/0195863 A1* | 8/2011 | Lifton et al. ...................... 506/9 |
| 2014/0127126 A1* | 5/2014 | Lifton et al. ................. 424/1.11 |

FOREIGN PATENT DOCUMENTS

WO    0218650    3/2002

OTHER PUBLICATIONS

Database UniProt [Online] "SubName: Full=Potassium inwardly-rectifying channel KCNJ10; Flags: Fragment;" XP002667142; Feb. 1, 2005.
Database UniProt [Online] "SubName: Full=Inward-rectifying potassium channel KCNJ10; Flags: Fragment;" XP002667143; Oct. 1, 2003.
Naegelin Y et al. "Off-label use of rituximab in patients with multiple sclerosis" Multiple Sclerosis, Sage Publications, Basingstoke, GB. vol. 15, No. 9, Sep. 1, 2009.
Berger, Joseph R. "Functional improvement and symptom management in multiple sclerosis: clinical efficacy of current therapies" The American Journal of Manages Care, US, vol. 17, no. Suppl. 5, May 1m 2011, pp. S146-S153.
O'Connor, et al. "Disease activity return during natalizumab treatment interruption in patients with multiple sclerosis," Neurology, Lippincott William & Wilkins, Philadelphia, US, vol. 76, No. 22, May 31, 2011, pp. 1858-1865.
International Search Report for International Application No. PCT/EP2012/059622, dated Nov. 9, 2012.

* cited by examiner

*Primary Examiner* — Jacob Cheu
(74) *Attorney, Agent, or Firm* — DT Ward, PC; Donna T. Ward; Lingyun Jia

(57) ABSTRACT

This invention relates to a peptide or a corresponding peptidomimetic that binds to an anti-KIR4.1 antibody in a sample from a patient, wherein said patient having multiple sclerosis or a predisposition therefor. The present invention furthermore relates to a method for diagnosing multiple sclerosis or a predisposition for multiple sclerosis in a subject, the method comprising determining the presence of an anti-KIR4.1 antibody in a sample obtained from said subject. Also provided are novel means and methods for the therapy of multiple sclerosis.

8 Claims, 9 Drawing Sheets b a

MEANS AND METHODS FOR DIAGNOSING AND TREATING MULTIPLE SCLEROSIS

CROSSREFERENCE TO RELATED APPLICATIONS

This application is a 35 U.S.C §371 U.S. National Stage Entry of International Application No. PCT/EP2012/059622 filed May 23, 2012, which claims the benefit of priority of EP Application No.: 11004423.7 filed May 30, 2011, the contents of which are each incorporated herein by reference in its entirety.

REFERENCE TO SEQUENCE LISTING

The present application is being filed along with a Sequence Listing in electronic format. The sequence Listing filed, entitled 206311000SequenceLst, was created on Nov. 26, 2013 and is 5,652 bytes in size. The information in electronic format of the Sequence Listing is incorporated herein by reference in its entirety.

FIELD OF THE INVENTION

This invention relates to a peptide comprising or consisting of at least 8 consecutive amino acid residues of the sequence set forth in SEQ ID NO: 3, provided that said peptide does not consist of the sequence set forth in SEQ ID NO: 3, or a corresponding peptidomimetic, wherein said peptide or peptidomimetic binds to an anti-KIR4.1 antibody comprised in a sample from a patient, said patient having multiple sclerosis or a predisposition therefor, wherein preferably (i) said at least 8 consecutive amino acid residues are a subsequence of an extracellular domain of KIR4.1, said extracellular domain consisting of the sequence set forth in SEQ ID NO: 1 or 2; or (ii) said peptide comprises or consists of the sequence of SEQ ID NO: 1 or 2. The present invention furthermore relates to a method for diagnosing multiple sclerosis or a predisposition for multiple sclerosis in a subject, the method comprising determining the presence of an anti-KIR4.1 antibody in a sample obtained from said subject, wherein the presence of an anti-KIR4.1 antibody in said sample is indicative of multiple sclerosis or a predisposition for multiple sclerosis.

BACKGROUND OF THE INVENTION

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Multiple sclerosis (MS) is the most common chronic inflammatory disease of the central nervous system (CNS) leading to disability in the majority of affected patients (1). The etiology of MS is unknown but epidemiological evidence suggests a complex interplay between genetic and environmental factors (2-4). An uncertain pathogenic mechanism, clinical heterogeneity and unpredictability of the outcome of individual patients add to the complexity of the disease (5).

The current working hypothesis for MS pathogenesis suggests that autoreactive T cells play a central role (6). However, histopathological studies have revealed a subset of MS patients exhibiting prominent deposition of immunoglobulins and complement activation in acute demyelinating lesions (7, 8). These patients respond particularly well to therapeutic plasma exchange (9). Moreover, B cell depletion by a therapeutic monoclonal antibody has a profound impact on inflammatory activity in MS (10). All these findings support the contention that at least in a subset of MS patients B cells and antibodies substantially contribute to the development and progression of the disease (11, 12). Despite this circumstantial evidence, a direct proof of clinically relevant antibodies in MS has not been established owing to the fact that specific molecular targets for humoral responses in MS remain undiscovered.

The technical problem can be seen in the provision of alternative or improved means and methods for diagnosing and/or treating multiple sclerosis.

DETAILED DESCRIPTION

The present invention provides in a first aspect a peptide comprising or consisting of at least 8 consecutive amino acid residues of the sequence set forth in SEQ ID NO: 3, provided that said peptide does not consist of the sequence set forth in SEQ ID NO: 3, or a corresponding peptidomimetic, wherein said peptide or peptidomimetic binds to an anti-KIR4.1 antibody comprised in a sample from a patient, said patient having multiple sclerosis or a predisposition therefor, wherein preferably (i) said at least 8 consecutive amino acid residues are a subsequence of an extracellular domain of KIR4.1, said extracellular domain consisting of the sequence set forth in SEQ ID NO: 1 or 2; or (ii) said peptide comprises or consists of the sequence of SEQ ID NO: 1 or 2. Accordingly, preferred are also peptidomimetics corresponding to the peptides according to options (i) and (ii). It is also preferred that said peptide does not comprise the sequence of SEQ ID NO: 3.

"KIR4.1" is a shorthand designation of a specific inward rectifying potassium channel. Preferably, said KIR4.1 is of human origin. The sequence of human KIR4.1 is provided in SEQ ID NO: 3. The terms "the sequence of human KIR4.1 protein" and "the sequence of SEQ ID NO: 3" are used herein to characterize the same entity.

The recited anti-KIR4.1 antibody is also referred to as "autoantibody" according to the invention. The autoantibody is a naturally occurring antibody and is preferably an IgG antibody. In particular, the autoantibody is the anti-KIR4.1 antibody occurring in MS patients and subjects having a predisposition for developing MS and is to be distinguished from any other anti-KIR4.1 antibodies which do not occur in said patients or subjects as well as further antibodies which may be used for therapeutic purposes as disclosed herein below. Said latter types of anti-KIR4.1 antibodies are not naturally occurring and not indicative of the disease. The autoantibody preferably binds to an extracellular domain of KIR4.1, said extracellular domain consisting of the sequence set forth in SEQ ID NO: 1 or 2. Preferably, said autoantibody binds to an extracellular domain consisting of the sequence set forth in SEQ ID NO: 1.

Preferred subsequences of the sequences of SEQ ID NOs: 1 and 2 are the sequences of SEQ ID NOs: 4 and 5, respectively. The sequences of SEQ ID NOs: 4 and 5 are expected to be extracellular in their entirety. Therefore, it is also preferred that said peptide comprises or consists of the sequence of SEQ ID NO: 4 or 5. Also, a peptidomimetic corresponding to the latter peptide is deliberately envisaged.

While peptides having sequences comprising or consisting of the sequence of any one of SEQ ID NOs: 1, 2, 4 or 5 are preferred, further peptide sequences are envisaged, wherein said peptide sequences may only partially or not at all overlap with the sequences of any one of SEQ ID NOS: 1, 2, 4 and 5.

To explain further, and as is known in the art, T-cells and B-cells may have different epitope preferences within a given antigen.

The term "peptide" refers to a polycondensate of amino acids. Preferably, said amino acids are selected from the 20 naturally occurring amino acids. The peptide according to the invention has a length of at least 8 amino acid residues. Preferred upper limits for the length of said peptide are 100, 50, 40, 30, 25, 20, 15, 14, 13, 12, 11, 10 or 9 amino acid residues and, in its broadest form, no upper length limit and accordingly includes polypeptides of any length. Preferably, the length of said peptide is chosen such that it is unique. As detailed further below, the length is preferably chosen such that the peptide is capable of binding to an MHC molecule. In particular, MHC I molecules are known to generally impose certain size limits on peptides being capable of binding thereto. Accordingly, preferred lengths and length ranges are from 8 to 12, from 8 to 10, and most preferred 9 amino acids. MHC II molecules on the other hand are generally capable of binding peptides of larger lengths as well and accordingly do not impose upper limits on the length of peptide according to the invention.

The term "peptidomimetics" is well-known in the art. It refers to derivatives of peptides, said derivatives being defined in structural terms further below. A "corresponding peptidomimetic" is a peptidomimetic which binds to the recited antibody. Such binding may be achieved by retaining structural features of each constituent amino acid of the peptide it is derived from, such parent peptide binding to the recited antibody as well. In a preferred embodiment, each of the side chains of said at least eight consecutive amino acid residues is retained in said corresponding peptidomimetic in modified or unmodified form. Side chain modifications include the replacement of one or more hydrogen atoms with halogen atoms, preferably F atoms. Further preferred side chain modifications include cyclisations. Independent thereof, one or more main chain peptide bonds may independently be replaced with functional groups which are isosteric or, in other words, mimic the peptide bond. Preferably, a peptide bond —CO—NH— may be replaced with any one of —NH—CO—, —CH—(OH)—CH2-, —CO—CH2-, —CH2-NH—, —CH2-O—, —CH2-CH2-, —CH=CH—, —CO—N(CH3)-, and PO2-X—, X preferably being selected from NH, O and CH2. As an example, in a corresponding peptidomimetic, all peptide bonds of the parent peptide may be replaced with retro-inverso bonds (—NH—CO—).

It is understood that substantially unaltered functional properties of the parent peptide are inherent to a peptidomimentic of the invention. In particular, a corresponding peptidomimetic binds to an anti-KIR4.1 antibody comprised in the sample of a patient with multiple sclerosis. Such binding can be assessed without further ado using means and methods described herein.

It is understood that the first aspect of the present invention relates to a peptide on the one hand, and, in the alternative, to a peptidomimetic. The disclaimer removes the amino acid sequence consisting of the sequence set forth in SEQ ID NO: 3 from the definition of the peptide. In other words, the first aspect relates to (a) a peptide comprising or consisting of at least 8 consecutive amino acid residues of the sequence set forth in SEQ ID NO: 3, provided that said peptide does not consist of the sequence set forth in SEQ ID NO: 3, or (b) a corresponding peptidomimetic, wherein said peptide or peptidomimetic binds to an anti-KIR4.1 antibody comprised in a sample from a patient, said patient having multiple sclerosis or a predisposition therefor, wherein preferably (i) said at least 8 consecutive amino acid residues are a subsequence of an extracellular domain of KIR4.1, said extracellular domain consisting of the sequence set forth in SEQ ID NO: 1 or 2; or (ii) said peptide comprises or consists of the sequence of SEQ ID NO: 1 or 2.

The peptide or peptidomimetic according to the invention bind to an anti-KIR4.1 antibody, wherein said anti-KIR4.1 antibody is comprised in a sample of a patient with multiple sclerosis (MS) or a subject having a predisposition to develop MS. As further detailed below, the present invention provides various means and methods for determining whether an MS patient carries anti-KIR4.1 autoantibodies as well as for isolating such antibodies from an MS patient. Said means include the agents generally referred to as "receptors" herein. Methods for isolating autoantibodies according to the invention include the step of bringing into contact said receptors with a sample obtained from a subject, the sample being suspected of containing anti-KIR4.1 antibodies. Using such anti-KIR4.1 antibodies obtained from an MS patient, the skilled person can determine without further ado whether a peptide comprising or consisting of at least 8 consecutive amino acid residues of KIR4.1 or a corresponding peptidomimetic is capable of binding to the antibody or not. A preferred means the skilled person can use is an ELISA assay. In such an assay, said peptide or peptidomimetic according to the main embodiment is immobilized on a carrier, the autoantibody from an MS patient or a subject having a predisposition for MS is allowed to bind the peptide or peptidomimetic, and said binding is detected by means of a secondary antibody which in turn is enzyme-linked. Said secondary antibody may, for example, be an antibody capable of binding FC fragments and accordingly would bind the FC part of the autoantibody.

Related to the above, the present invention furthermore provides an anti-KIR4.1 antibody obtainable from a multiple sclerosis patient or a subject having a predisposition to develop MS. This is the autoantibody defined herein above.

As described in more detail in the examples enclosed herewith, at least two extracellular domains are present in KIR4.1. The two extracellular domains are also referred to as large and small extracellular domain. An anti-KIR4.1 antibody indicative of multiple sclerosis preferably binds to the large extracellular domain, the small extracellular domain or both extracellular domains. The sequences of large and small extracellular domain of KIR4.1, respectively, are provided in SEQ ID NOs: 1 and 2. The strictly extracellular parts thereof are provided in SEQ ID NOs: 4 and 5, respectively.

The term "multiple sclerosis" refers to an inflammatory disease affecting the nervous system; see also the literature quoted in the background section above. Whether or not a subject or patient has multiple sclerosis can be determined with the method of diagnosing according to the invention which is subject of the second aspect of the invention and described further below. Alternatively or in addition, a diagnosis of multiple sclerosis can be established on the basis of established clinical symptoms, said clinical symptoms being known to the skilled person. The clinical symptoms of multiple sclerosis include vision problems, dizziness, vertigo, sensory dysfunction, weakness, problems with coordination, loss of balance, fatigue, pain, neurocognitive deficits, mental health deficits, bladder dysfunction, bowel dysfunction, sexual dysfunction, heat sensitivity.

While a detection of anti-KIR4.1 autoantibodies in a sample taken from a patient or a subject indicates multiple sclerosis or a predisposition therefor, it has to be understood that multiple sclerosis or a predisposition therefor is not necessarily characterized in that said autoantibodies are present in said subject or patient or a sample taken therefrom.

Accordingly, the presence of anti-KIR4.1 autoantibodies defines a subgroup of individuals having a predisposition to develop MS, said subgroup being characterized in that they have said autoantibodies. Similarly, a subgroup of MS patients is disclosed herein, said subgroup being characterized in that they have said autoantibodies. In other terms, presence of the autoantibody defines a sub-indication within the indication which is multiple sclerosis. It is expected that patients exhibiting this sub-indication of MS respond differently to treatment when compared to MS patients which do not have said autoantibodies. Similarly, it is expected that the risk profile of subjects having said autoantibodies differs from the risk profile of subjects which do not have said autoantibodies. As a consequence, different curative treatments as well as different preventive treatments may be chosen in dependence of whether an MS patient has autoantibodies or not, and whether a subject at risk of developing MS has said autoantibodies or not, respectively.

The term "subsequence" refers to a stretch of contiguous amino acid residues taken from a larger sequence. In other words, if said larger sequence consists of n residues, the maximal length of a subsequence is (n−1) residues.

The present invention furthermore provides a nucleic acid encoding the above defined peptide according to the invention. The nucleic acid may be DNA, such as cDNA or genomic DNA, or RNA. Furthermore provided is a vector comprising said nucleic acid. Moreover, the present invention relates to a host cell comprising a nucleic acid and/or vector according to the invention. The host cell may be of any origin and is preferably in vitro such as isolated or in culture. While it is noted that human embryonic stem cell lines are at the skilled person's disposal, it is preferred that the host cell is not obtained by using or destroying human embryos. Also, it is preferred that the host cell, to the extent it is an embryonic cell or an embryonic stem cell, is non-human.

In a second aspect, the present invention provides a method for diagnosing multiple sclerosis or a predisposition for multiple sclerosis in a subject, the method comprising determining the presence of an anti-KIR4.1 antibody in a sample obtained from said subject, wherein the presence of an anti-KIR4.1 antibody in said sample is indicative of multiple sclerosis or a predisposition for multiple sclerosis.

This method permits to diagnose multiple sclerosis, or, to the extent multiple sclerosis is not apparent in said subject, for diagnosing a predisposition therefor. The term "predisposition" has the meaning as established in the art and prefers a likelihood to develop a disease. In particular, said likelihood is higher than in a normal control subject. Said likelihood in a normal control subject may be represented as the average likelihood to develop MS in a random sample from the population.

Suitable agents for determining said presence of an anti-KIR4.1 antibody are described further below, in particular as active agents in relation to the disclosed diagnostic compositions and diagnostic uses.

A preferred group of individuals to be tested for said predisposition are individuals with a history of MS in the family.

The present inventors are the first ones to identify a molecular target of the previously suspected autoimmune response in MS. It is noteworthy that conventional strategies to uncover autoantibodies in MS have largely focused on serological screening for immunoglobulins to preselect candidate target molecules based on their functional relevance to myelin biology and encephalitogenic potential in animal models (13). Also, *E. coli* expression, phage display and peptide libraries were screened to identify linear targets of MS specific autoantibodies (14-17). Neither strategy has yet yielded any potential targets that could either be MS-specific or prognostic (18, 19).

The present inventors detected high titers of anti-KIR4.1 antibodies in patient sera of 50.8% of two independent cohorts. Accordingly, the means and methods described herein allow diagnosis of MS or a predisposition therefor in about half of the MS cases or subjects being at risk to develop the disease, respectively. In particular, the methods of the invention permit early diagnosis of MS or a predisposition therefor or a confirmation of an uncertain diagnosis. The antibody test may allow to diagnose CIS or MS without invasive procedures (such as cerebrospinal fluid analysis) and to diagnose MS, CIS or predisposition to MS earlier than this would be possible by diagnostic procedures known in the art. "CIS" refers to "clinically isolated syndrome" and is discussed further below. It is well known that MS therapy works best when started as early as possible during the course of disease. Therefore early diagnosis may allow to implement early treatment of patients with CIS, MS or at risk to develop these diseases. In some individuals at risk treatment may even prevent the (further) development of disease.

As shown in the Examples enclosed herewith, the autoantibodies may deplete KIR4.1 expressing glial cells via antibody dependent cell-mediated cytoxicity (ADCC) or complement activation (FIG. 6). In addition, the antibody may interfere with the function of the potassium channel resulting in functional consequences for ion buffering and neurotransmitter homeostasis (20, 21, 22). This may result in tissue injury or impaired remyelination.

In a preferred embodiment of the methods according to the invention, and in case an anti-KIR4.1 antibody is present in said sample, (i) presence of at least one clinical symptom of multiple sclerosis in said subject is indicative of multiple sclerosis; and (ii) absence of any clinical symptom of multiple sclerosis is indicative of said predisposition for multiple sclerosis.

As disclosed above, the methods according to the invention provide for diagnosing multiple sclerosis as well as for diagnosing a predisposition therefor. The present preferred embodiment provides for further information to be acquired for said subject, said further information aiding in distinguishing between diagnosis of the disease and diagnosis of a predisposition therefor. In particular, said further information consists of or comprises at least one clinical symptom of multiple sclerosis. Multiple sclerosis is a well-known disease with established clinical symptoms. The skilled person is well aware of clinical symptoms being characteristic or indicative of multiple sclerosis (see also further below) and can determine the presence or absence thereof without further ado.

In accordance with the present preferred embodiment, the absence of any clinical symptom of multiple sclerosis, when concomitantly occurring together with the presence of anti-KIR4.1 antibodies, is indicative of predisposition for multiple sclerosis. In other words, where established methods of diagnosis or prognosis fail, the present invention allows to identify those subjects which exhibit an elevated risk of developing multiple sclerosis at some point in the future.

On the other hand, in subjects where at least one clinical symptom of multiple sclerosis is present, the determination of anti-KIR4.1 antibodies further corroborates the diagnosis of multiple sclerosis. In those cases where the clinical parameters alone do not permit a clear diagnosis, the present invention aids in performing and substantiating said diagnosis. This applies in particular to early forms of multiple sclerosis. As is well-known in the art, an early diagnosis of multiple sclerosis is highly desirable, given that early stages are generally more amenable to treatment.

According to a further preferred embodiment, said clinical symptom is at least one selected from vision problems, dizziness, vertigo, sensory dysfunction, weakness, problems with coordination, loss of balance, fatigue, pain, neurocognitive deficits, mental health deficits, bladder dysfunction, bowel dysfunction, sexual dysfunction, heat sensitivity, the presence of (an) inflammation marker(s) in cerebrospinal fluid (CSF), the presence of lesions of the brain and/or the spinal cord. The mentioned lesions may be detected in an MRT image. Typically, such lesions occur in the periventricular, juxtacortical and/or infratentorial region of the brain. Inflammation markers indicative of MS are well-known in the art and are preferably to be selected from pleocytosis (abnormally increased number of cells in the CSF, wherein typical values of increased cell numbers are between 5 and 50 cells/µl or above), intrathecal IgG synthesis and the occurrence of oligoclonal IgG bends in the CSF.

According to a further preferred embodiment, said subject has clinically isolated syndrome (CIS), or said at least one clinical symptom is CIS. CIS is generally perceived in the art as being an early stage of MS, wherein the clinical parameters characteristic of the latter are not yet fully developed. For a discussion of CIS, see, for example, Thrower, Neurology 68, S12-S15 (2007). The means and methods according to the present invention are advantageous in that they permit collection of further evidence for those patients which have CIS.

According to a further preferred embodiment, said anti-KIR4.1 antibody, i.e., the anti-KIR4.1 antibody which may occur in MS patients as well as subjects being at risk to develop MS, binds to KIR4.1 (SEQ ID NO: 3) or an extracellular domain of KIR4.1 consisting of the sequence set forth in any one of SEQ ID NOs: 1, 2, 4 or 5. The structure of KIR4.1 is further described in the examples enclosed herewith. In particular, it comprises (at least) two extracellular domains which are presumably separated by one transmembrane spanning segment; see FIG. 4c. The two extracellular domains are herein also referred to as large extracellular domain and small extracellular domain and are set forth in SEQ ID NOs: 1 and 2. The residue ranges indicated in FIG. 4c are those of SEQ ID NOs: 4 and 5, respectively.

In a further preferred embodiment, the detection of the anti-KIR4.1 antibody in said sample is effected by a method selected from the group consisting of ELISA, immunoprecipitation, Western blotting, immunofluorescence, immunohistochemistry, flow cytometry, metalloimmunoassay (such as GLORIA), fluorescence resonance energy transfer (FRET) assay and mass spectroscopy. These methods are well-established and at the skilled person's disposal. For example, in an ELISA assay, an antibody binding to said anti-KIR4.1 antibody may be used. Similar considerations apply to immunoprecipitation, Western blotting, immunofluorescence and immunohistochemistry. As noted above, the skilled person, when provided with the teaching of the present invention, can isolate and characterize the anti-KIR4.1 antibody without further ado. Such characterization preferably uses mass spectrometry. Once being characterized, mass spectrometry may be used for determining presence or absence of anti-KIR4.1 antibodies in any given sample. FRET assays may be used, for example, in the context of a binding assay, said binding assay preferably making use of a receptor, said receptor being defined further below. Such FRET assay may be designed such that a detectable transfer between donor and acceptor of the FRET pair only occurs in case receptor and anti-KIR4.1 antibody are in close special proximity, said close special proximity being indicative of the presence of the anti-KIR4.1 antibody.

In further preferred embodiments, the presence of said anti-KIR4.1 antibody is determined by (a) contacting the sample with a receptor binding to said anti-KIR4.1 antibody; and (b) detecting the formation of a receptor-anti-KIR4.1 antibody complex, wherein said receptor is preferably selected from the group consisting of a peptide or peptidomimetic according to the invention, KIR4.1 protein (SEQ ID NO: 3) and an antibody binding to said anti-KIR4.1 antibody. As described further below, means and methods for preparing an antibody against a given antigen (including an antibody) are at the skilled person's disposal.

Whereas the previous preferred embodiment provides various readout schemes, the present preferred embodiment provides specific means for effecting detection of anti-KIR4.1 antibodies, said specific means being characterized in structural terms. Accordingly, these preferred embodiments—as well as any other embodiments disclosed herein—are amenable to combination if not indicated otherwise, any of said combinations being the subject of further preferred embodiments according to the present invention. In a preferred assay, KIR4.1 protein is expressed in cells, said cells are incubated with serum, and binding of the autoantibody to KIR4.1 protein is determined by means of flow cytometry or immunohistochemistry using a secondary antibody. As stated above, said secondary antibody preferably binds to said autoantibody, for example by binding to the FC part thereof. Further preferred assays are described in the examples enclosed herewith.

Preferred embodiments of the recited receptor are a peptide or peptidomimetic according to the invention and an antibody binding to said anti-KIR4.1 antibody. In either case, it is furthermore preferred that said receptor is specific for said anti-KIR4.1 antibody. Specificity can be determined in comparative or competition assays, wherein binding of the receptor to said anti-KIR4.1 antibody on the one hand and to other proteins, binding proteins or antibodies is determined. Preferably, the binding constant (Kd) of the receptor for the autoantibody is at least one order of magnitude, preferably at least two, three, four, five or six orders of magnitude lower than for the other proteins tested. An "order of magnitude" is a factor of 10.

Therapeutic or diagnostic antibodies as disclosed herein may be monoclonal or polyclonal antibodies. Furthermore, and in particular in the context of diagnostic and therapeutic antibodies as disclosed herein, the term "antibody" furthermore includes single chain antibodies or fragments thereof that specifically bind to their respective target as well as bispecific antibodies, synthetic antibodies, antibody fragments such as Fab, F(ab2)', Fv and scFv fragments and the like as well as chemically modified derivatives thereof.

Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the peptide or polypeptide of the invention (Schier, Human Antibodies Hybridomas 7 (1996), 97-105; Malmborg, J. Immunol. Methods 183 (1995), 7-13). The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning: A Laboratory Manual, Cold Spring Harbor Laboratory, Cold Spring Harbor, N.Y., 1989.

The term "monoclonal" or "polyclonal antibody" (see Harlow and Lane, (1988), loc. cit.) also relates to derivatives of said antibodies which retain or essentially retain their binding specificity. Whereas particularly preferred embodiments of said derivatives are specified further herein below, other preferred derivatives of such antibodies are chimeric antibodies comprising, for example, a mouse or rat variable region and a human constant region.

The term "scFv fragment" (single-chain Fv fragment) is well understood in the art and preferred due to its small size and the possibility to recombinantly produce such fragments.

In a particularly preferred embodiment of the method of the invention, said antibody or antibody binding portion is or is derived from a human antibody or a humanized antibody. The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A 1 0 239 400 and WO90/07861.

In a further preferred embodiment, said sample is selected from blood, serum, plasma, lymph nodes, CSF, lacrimal fluid, urine, sputum and brain biopsy.

In a third aspect, the present invention provides a receptor as defined above for use in the treatment of multiple sclerosis or in the diagnosis of multiple sclerosis or a predisposition therefor. The receptor as defined herein above as well as the entire KIR4.1 protein (i.e. the protein consisting of the sequence set forth in SEQ ID NO: 3) are envisaged for these medical uses. The administration of these agents serves to reduce the number of circulating anti-KIR4.1 antibodies. As will be described in more detail below, these agents may not only be administered to a patient suffering from MS or to a subject having or being suspected of having a predisposition therefor, but may also be used in ex vivo methods, said ex vivo methods providing for the removal of the autoantibodies from an MS patient or, more specifically, from a bodily fluid of said patient or a subject at risk to develop MS.

The term "treatment" refers to treatment by therapy and embraces amelioration of the disease and/or its symptoms as well as complete remission. Furthermore, the term "treatment" extends to prevention.

In preferred embodiments of the medical uses according to the present invention, one or more of the recited agents are the only active agents to be used. In alternative preferred embodiments, one or more of said explicitly recited agents may be used in conjunction with one or more of agents known to be beneficial to MS patients or known to aid in diagnosis of MS. Until now, progression of MS is prevented or mitigated and relapses are prevented by administration of one or more of the following: Interferon-beta, Glatirameracetate, Natalizumab, Mitoxantrone, Fingolimod, Azathioprine. Relapses are treated with high doses of Methlprednisolone and/or plasma exchange treatment.

In preferred embodiments, said receptor is to be contacted with blood, serum, plasma, lymph nodes, CSF, lacrimal fluid, urine, sputum and/or brain biopsy obtained from a subject. This embodiment refers to preferred samples which are to be used in diagnosis.

In a further preferred embodiment of the third aspect of the invention, to the extent said third aspect relates to therapy, said receptor is to be administered to the patient at least two times. Multiple administration provides for high degrees of removal, preferably complete removal of autoantibodies and eventually for amelioration or remission of the disease.

In a further preferred embodiment, said peptide may be chosen such that it binds to an MHC allele of the patient to be treated. Said MHC molecule may be an MHC class I or class II molecule. In order to ensure binding to an MHC class I molecule, it is preferred that said peptide consists of 8 to 12, preferably of 8 to 10 and most preferred of 9 amino acids. Furthermore, it is preferred that anchor amino acid residues, said anchor amino acid residues being residues known to be involved in MHC binding, are present. Selection of suitable peptide sequences within the SEQ ID NOs: 1 and 2 are well within the skills of the skilled person. For example, Rammensee et al. (Immunogenetics, 41: 178-228, 1995) describes features including anchor amino acids of MHC binding peptides. Presenting of said peptide in an MHC context allows to target an additional or alternative mechanism in the treatment or prevention of MS. More specifically, it permits the drive T-cells specific for KIR4.1 into apoptosis, thereby reducing or abolishing the autoimmune reaction to endogenous KIR4.1 protein. In a yet further preferred embodiment, MHC-peptide complexes for use in the treatment of multiple sclerosis are provided. Particularly preferred is the use of MHC multimers such as MHC tetramers, wherein preferably each MHC molecule has a peptide or peptidomimetic according to the invention bound. Preferably, said peptide or peptidomimetic is the same for all MHC molecules of said multimer or tetramer. As is known in the art, tetramer formation may be achieved by using biotinylated MHC molecules. The carboxy terminus of an MHC molecule is a preferred target of biotenylation. When incubated with a streptavidin, tetramers are formed because streptavidin has four biotin binding sites. Such multimers or tetramers bind antigen-specific T-cell receptors with particularly high affinity. Therefore, use of multimers, preferably tetramers of peptide bound MHC molecules permits identification and furthermore inactivation of KIR4.1-specific T-cells.

Furthermore, and without being bound by specific theory, it is envisaged that the administration of peptides or peptidomimetics according to the invention permits desensitisation of T-cells and B-cells responsible for the disease. In this regard, one or more positions of said peptide or peptidomimetic, said positions interacting with the T-cell receptor, may be modified for the purpose of fine-tuning T-cell receptor interaction of said peptide or peptidomimetic. Such positions and approaches for their modification are known in the art; see, for example, Kappos et al., Nature Med. 6, 1176-1182 (2000).

In other words, the invention provides means and methods for induction of tolerance of KIR4.1. The term "tolerance" has the meaning as established in the art and refers to a non-reactivity of the immune system to a given antigen. Typically, there is tolerance with regard to self antigens. In the absence of tolerance to a self antigen, autoantibodies may be generated and an autoimmune disease may arise. As is apparent from the disclosure of this invention, multiple sclerosis has characteristics of an autoimmune disease. In order to reduce or abolish the generation of autoantibodies against the KIR4.1 protein, induction of tolerance or desensitisation is one of the preferred approaches. The envisaged effect is the establishment of self-tolerance with regard to KIR4.1. Since tolerance is an antigen-dependent effect, it can exist in B-cells, T-cells or both B-cells and T-cells. The phenomenon of tolerance as such as well as the mechanisms underlying B-cell and T-cell tolerance are known in the art.

In a fourth aspect, the present invention provides an antibody binding to KIR4.1 (SEQ ID NO: 3) or an extracellular domain of KIR4.1 for use in the treatment of multiple sclerosis, said domain consisting of the sequence set forth in SEQ ID NO: 1 or 2, and said antibody interfering with the binding to KIR4.1 of an anti-KIR4.1 antibody comprised in a sample from a patient, said patient having multiple sclerosis or a predisposition therefor.

Preferably, said antibody binding to an extracellular domain of KIR4.1 is specific therefor. Means and methods for determining specificity of antibodies are at the skilled person's disposal and described herein above. It is particularly preferred that the above antibody to be used in therapy is capable of binding to an epitope which is not recognized by any autoantibody. In this regard, it is noted that means and methods for epitope mapping are at the skilled person's disposal. By choosing an appropriate epitope, the above mentioned functional requirements, i.e., interference with binding of the autoantibodies, can be ensured. It is furthermore preferred that binding of the therapeutic antibody does not or not significantly interfere with the biochemical or cellular function of KIR4.1. KIR4.1 is known to be involved in homeostasis of water and potassium ions in the central nervous system. Maintaining or re-establishing the function of KIR4.1 is therefore envisaged to exhibit a protective effect for neurons and clear cells.

These embodiments provide means of interfering with binding of the autoantibodies to their cognate target and thereby alleviating the disease.

In a fifth aspect, the present invention provides a composition comprising (i) a peptide of the invention, (ii) an antibody binding to an anti-KIR4.1 antibody as defined above (i.e., an antibody binding to an autoantibody), and/or (iii) an antibody of the preceding embodiments, i.e., an antibody interfering with the binding of the autoantibody to its target.

Accordingly, the present disclosure refers to three distinct types of antibodies. First, there is disclosure of the autoantibody binding to an extracellular loop of KIR4.1. This is the antibody considered causative and/or indicative of MS in about half of the MS patients. Secondly, the invention provides an antibody capable of binding to the autoantibody. This second type of antibody is suitable for both therapeutic and diagnostic purposes detailed herein above. Finally, the invention provides an antibody which binds to KIR4.1 and at the same time interferes with the binding of the autoantibody to its target. This latter antibody is suitable for therapeutic purposes described herein above.

Preferred embodiments of the composition according to the invention relate to a pharmaceutical composition optionally further comprising a pharmaceutically acceptable carrier and/or diluent, and, to the extent said composition relates to a peptide or antibody binding to an anti-KIR4.1 antibody, to a diagnostic composition. Suitable pharmaceutically acceptable carriers, excipients, and/or diluents can be chosen by the skilled person without further ado. For example, the antibody may be provided in solution such as buffered solution.

Buffers are well known in the art and the skilled person is aware of appropriate buffers in dependency of the substances being assayed. Common buffers comprise (pKa values in brackets) $H_3PO_4/NaH_2PO_4$ ($pKa,1=2.12$), Glycine ($pKa,1=2.34$), Acetic acid (4.75), Citric acid (4.76), MES (6.15), Cacodylic acid (6.27), $H_2CO_3/NaHCO_3$ ($pKa,1=6.37$), Bis-Tris (6.50), ADA (6.60), Bis-Tris Propane ($pKa,1=6.80$), PIPES (6.80), ACES (6.90), Imidazole (7.00), BES (7.15), MOPS (7.20), $NaH_2PO_4/Na_2HPO_4$ ($pKa,2=7.21$), TES (7.50), HEPES (7.55), HEPPSO (7.80), Triethanolamine (7.80), Tricine (8.10), Tris (8.10), Glycine amide (8.20), Bicine (8.35), Glycylglycine ($pKa,2=8.40$), TAPS (8.40), Bis-Tris Propane ($pKa,2=9.00$), Boric acid ($H_3BO_3/Na_2B_4O_7$) (9.24), CHES (9.50), Glycine ($pKa,2=9.60$), $NaHCO_3/Na_2CO_3$ ($pKa,2=10.25$), CAPS (10.40) and $Na_2HPO_4/Na_3PO_4$ ($pKa,3=12.67$).

Furthermore, ionic strength of said buffer may be adjusted, e.g., by the addition of sodium chloride and/or potassium chloride. Preferred concentrations of sodium chloride are between 0 and 2 M, preferably between 100 and 200 mM. Examples of buffers comprising sodium chloride include PBS (phosphate buffered saline) containing 1.37 M NaCl, 27 mM KCl, 43 mM $Na_2HPO_4.7H_2O$ and 14 mM $KH_2PO_4$ in the 10-fold aqueous stock solution, which is adjusted to pH 7.3; SSC containing 3 M NaCl and 0.3 M sodium citrate in 20-fold aqueous stock solution, which is adjusted to pH 7.0; and STE (Saline Tris EDTA) containing 10 mM Tris base, 10 mM NaCl and 1 mM ETA (acid). Alternatively, sodium chloride is absent from the buffer preparation. Examples for common buffer preparations without sodium or potassium chloride are TAE (Tris acetate EDTA) containing 2 M Tris acetate and 0.1 M EDTA in the 50-fold aqueous stock solution at pH 8.5; TBE (Tris borate EDTA) containing 0.89 M Tris base, 0.89 M Boric acid and 0.02 M EDTA in the 10-fold aqueous stock solution at pH 8.0; and TE (Tris EDTA) containing 10 mM Tris base and 1 mM EDTA (acid) at pH 7.5.

The pharmaceutical compositions described herein can be administered to the subject at a suitable dose. Administration of the suitable compositions may be effected by different ways, e.g., by intravenous, intraperitoneal, subcutaneous, as well as transdermal administration.

More specifically, the pharmaceutical compositions may be administered orally, parenterally, such as subcutaneously, intravenously, intramuscularly, intraperitoneally, intrathecally, transdermally, transmucosally, subdurally, nasal, locally or topically via iontophoresis, sublingually, by inhalation spray, aerosol or rectally and the like in dosage unit formulations optionally comprising conventional pharmaceutically acceptable excipients.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition described herein may comprise further agents depending on the intended use of the pharmaceutical composition.

Pharmaceutically useful excipients that may be used in the formulation may comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colourants, flavours, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, and/or ion exchange resins.

Other suitable pharmaceutically acceptable excipients are described in Remington's Pharmaceutical Sciences, 15th Ed., Mack Publishing Co., New Jersey (1991).

Dosage forms for oral administration include tablets, capsules, lozenges, pills, wafers, granules, oral liquids such as syrups, suspensions, solutions, emulsions, powder for reconstitution.

Dosage forms for local/topical administration comprise insufflations, aerosols, metered aerosols, transdermal therapeutic systems, medicated patches, rectal suppositories, and/or ovula.

For the purpose of the present invention, a therapeutically effective dosage of the recited agents may generally be from about 2.5 to 100 mg/day, preferably from about 5 to about 50 mg/day, and most preferably from about 10 to about 30 mg/day, which may be administered in one or multiple doses.

It will be appreciated, however, that specific dose level of the compounds of the invention for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgement of the ordinary clinician or physician.

In a sixth aspect, the present invention provides an agent selected from Rituximab, Ocrelizumab, Ofatumumab and an FC-binding agent for use in the treatment of multiple sclerosis in a patient, said patient being characterized by the presence of anti-KIR4.1 antibodies in any one of blood, serum, plasma, lymph nodes, cerebrospinal fluid (CSF), lacrimal fluid, urine, sputum and brain biopsy. As explained herein above, it is expected that MS patients with autoantibodies on the one hand and MS patients without autoantibodies on the other hand respond differently to these agents.

FC-binding agents are known agents suitable for the removal of antibodies. Such agents bind to the FC part of antibodies and are suitable for the removal or inactivation of antibodies. Such process of removal is also referred to as immunoadsorption.

In a seventh aspect, the present invention furthermore provides a method of screening for a drug or lead compound, said method comprising: bringing into contact a complex comprising or consisting of (i) an anti-KIR4.1 antibody as defined above (i.e., an autoantibody); and (ii) KIR4.1 protein or a peptide or peptidomimetic as defined above with a test compound, wherein a reduction of the amount of said complex is indicative of the test compound being a drug or lead compound.

In view of the surprising discovery that anti-KIR4.1 antibodies are involved in multiple sclerosis, the present invention furthermore provides for means and methods of identifying drugs and lead compounds, said drugs and lead compounds being suitable for the treatment or for the development of drugs suitable for the treatment of multiple sclerosis. It is understood that the recited bringing into contact is effected under conditions which maintain said complex. The skilled person is aware of such suitable conditions which include, for example, buffered solutions comprising the test compound, an anti-KIR4.1 antibody, and KIR4.1 protein or a peptide or peptidomimetic according to the invention.

Preferably, said method is effected in high-throughput format. High-throughput assays, independently of being biochemical, cellular or other assays, generally may be performed in wells of microtiter plates, wherein each plate may contain 96, 384 or 1536 wells. Handling of the plates, including incubation at temperatures other than ambient temperature, and bringing into contact of test compounds with the assay mixture is preferably effected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits biological activity, said mixture of test compounds may be de-convoluted to identify the one or more test compounds in said mixture giving rise to said activity.

Test compounds, lead compounds and/or drugs are preferably small molecules, more preferred small organic molecules. The molecular weight is preferably below 2000, more preferred below 1500, 1000, 900, 800, 700, 600, 500 or 400 Daltons. Any hit identified in the screen may be subjected to an optimization of its pharmacological properties (including absorption, distribution, metabolism and excretion), thereby developing the lead compound into a drug.

Methods for the optimization of the pharmacological properties of compounds identified in screens, generally referred to as lead compounds, are known in the art and comprise a method of modifying a compound identified as a lead compound to achieve: (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmacokinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii)

esterification of hydroxyl groups with carboxylic acids, or (iii) esterification of hydroxyl groups to, e.g. phosphates, pyrophosphates or sulfates or hemi-succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiff's bases, oximes, acetales, ketales, enolesters, oxazolidines, thiazolidines or combinations thereof.

The various steps recited above are generally known in the art. They include or rely on quantitative structure-action relationship (QSAR) analyses (Kubinyi, "Hausch-Analysis and Related Approaches", VCH Verlag, Weinheim, 1992), combinatorial biochemistry, classical chemistry and others (see, for example, Holzgrabe and Bechtold, Deutsche Apotheker Zeitung 140(8), 813-823, 2000).

The present invention, in an eighth aspect, provides the use of a receptor as defined above for removing anti-KIR4.1 antibodies from blood or serum or reducing the amount thereof, wherein said use is to be effected ex vivo.

Related thereto, the present invention provides an ex vivo method of removing anti-KIR4.1 antibodies from a bodily fluid such as blood or serum or reducing the amount thereof, said method comprising (a) bringing blood removed from a subject into contact with a receptor as defined above and/or an FC-binding agent; and/or (b) performing plasmapheresis.

These aspects relate to ex vivo applications, said ex vivo applications aiming at a reduction of a number of autoantibodies or a complete depletion thereof. Preferably, blood or serum of an MS patient or of a subject carrying a predisposition to develop MS are subjected to the ex vivo treatment. It is understood that said bringing into contact is effected under conditions which allow binding of autoantibodies, if present, to said receptor. In one embodiment, said conditions may be established by bringing into contact blood or serum with a carrier or device according to the invention, said carrier or device being further defined below. Plasmapheresis as such is known in the art and may be used, in accordance with the invention, to reduce the number of circulating autoantibodies.

In a preferred embodiment of the ex vivo method according to the invention, the blood or serum, after said bringing into contact, is to be returned to the same subject.

In further preferred embodiments of the ex vivo use or the ex vivo method of the invention, said protein, peptide and/or antibody is bound to a carrier. Any carrier, including a solid carrier is envisaged. Support or carrier materials commonly used in the art and comprising glass, plastic, gold and silicon are envisaged for the purpose of the present invention. Suitable coatings of the carrier or support, if present, include poly-L-lysine- and amino-silane-coatings as well as epoxy- and aldehyde-activated surfaces. In a preferred embodiment, said carrier is the matrix of a column. Suitable matrices are known in the art and may be derivatized by the attachment of said receptor.

The present invention furthermore relates to a carrier with a receptor as defined above being immobilized thereon.

Related thereto, provided is also a device for removing anti-KIR4.1 antibodies from blood, said device comprising the carrier as defined above.

In a preferred embodiment of the device, said device further comprises an inlet and/or an outlet permitting to let blood or serum of the subject flow across the filter and/or the blood or serum being returned to the same subject.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all attached claims. To give a few examples, the combination of claims 6, 5, 4(b), 3 and 2 is clearly and unambiguously envisaged in view of the claim structure. The same applies for the combinations of claims 6, 5, 4(a), 3 and 2, and, to give a few further examples which are not limiting, the combination of claim 4(a) and 2 and the combination of claim 5, 4(a) and 2.

(b) Capture ELISA assay with membrane protein fractions prepared from rat brain tissue. Serum reactivities in MS and OND patients are shown (OD, optical density).

Figure 2:
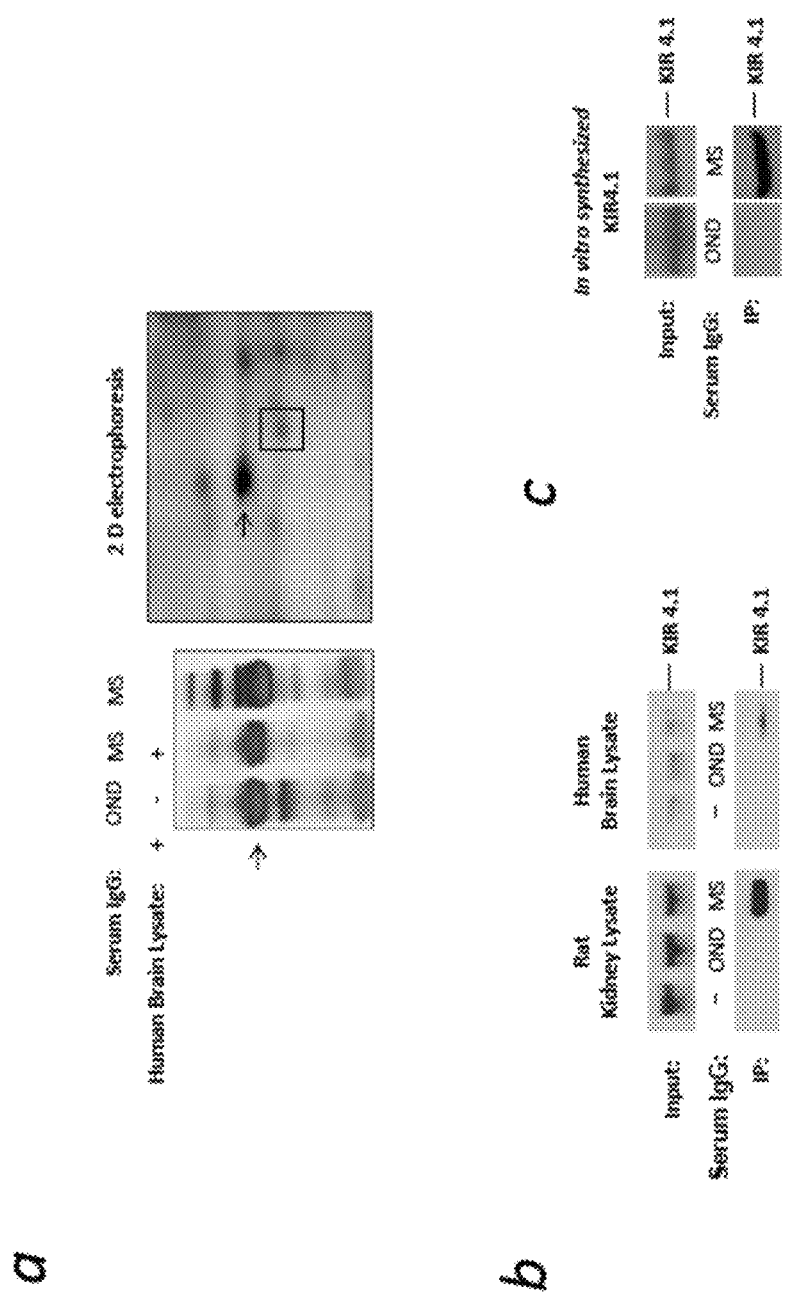

FIG. 2: Identification of KIR4.1 as target of serum IgG in MS (a) One dimensional SDS gel electrophoresis (left) of human brain lysate precipitated with pooled IgG from OND or MS patients. Note that unique bands (third lane) above and below the IgG heavy chain band (arrow) were obtained after immunoprecipitation with pooled serum IgG purified from MS patients. Two dimensional electrophoresis (right) of brain antigens obtained after immunoprecipitation with serum IgG from MS patients. The spot containing the KIR4.1 protein identified by MALDI-MS/MS analysis is marked with a frame. The arrow marks the IgG heavy chain spot.

(b) KIR4.1 detection by Western blot analysis in various immunoprecipitates as indicated. Immunoprecipitations were performed with serum IgG from OND or MS patients on enriched membrane protein fractions of rat kidney and human brain lysates, respectively.

(c) Western blot analysis of KIR4.1 in immunoprecipitates of in vitro translated KIR4.1 protein with serum IgG from OND or MS patients.

Figure 3:
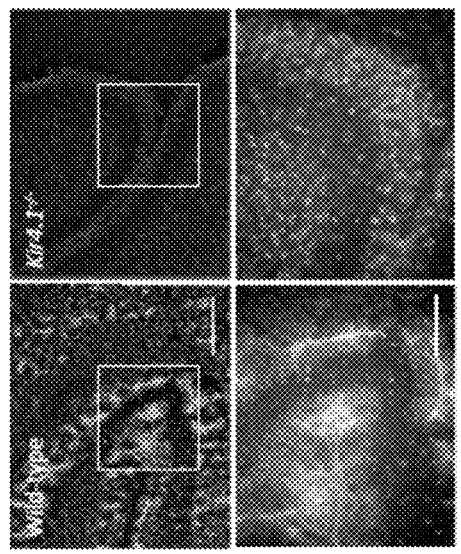
Figure 3:
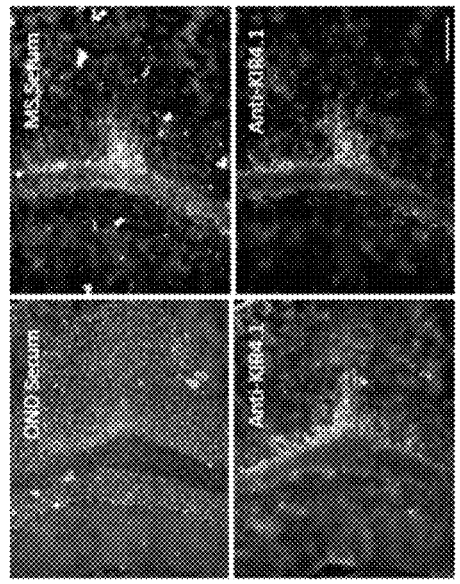
Figure 3:
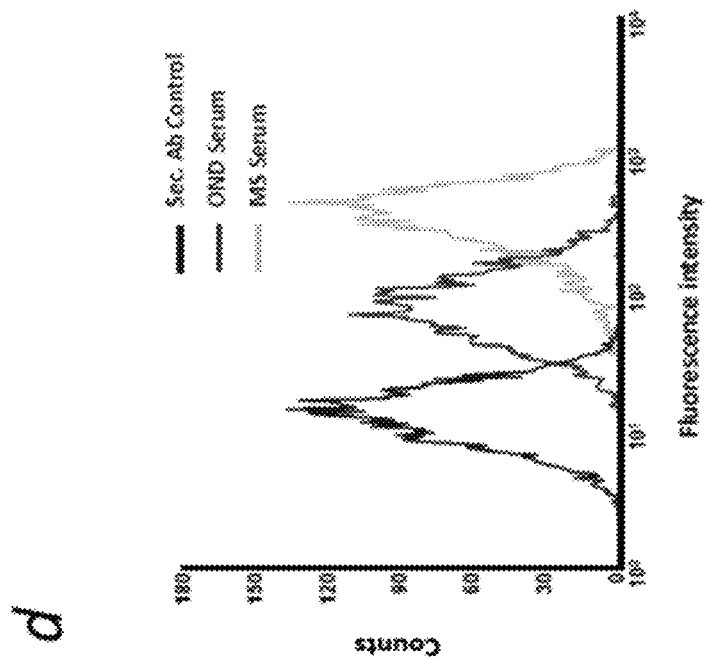
Figure 3:
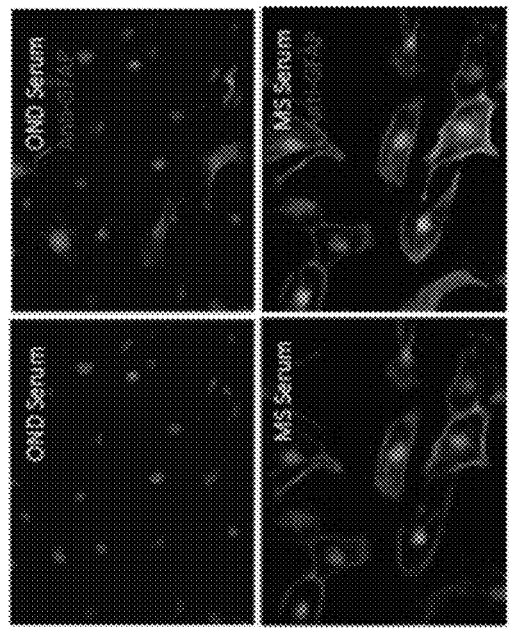

FIG. 3: Validation of KIR4.1 as the target of the serum IgG reactivity in MS patients (a) Double immunofluorescence labeling showing co-localization of serum IgG from an MS patient with monoclonal anti-KIR4.1 in rat brain cerebellum sections. Staining with serum of an OND patient is shown as control. Scale bar 200 μm.

(b) Immunofluorescence labeling of cerebellar sections of wild type (left panels) and Kir4.1−/− mice (right panels) with purified serum IgG from an MS patient. Scale bars 100 μm (upper panels) and 50 μm (lower panels).

(c) Double immunofluorescence staining of mouse primary astroglial cell cultures. Staining with OND serum IgG (upper panels) and MS serum IgG (lower panels) was detected in the green channel. Additional GFAP staining (right panels) was detected in the red channel.

(d) Staining and flow cytometric analysis of mouse primary astrocytes with serum from MS and OND patients.

Figure 4:
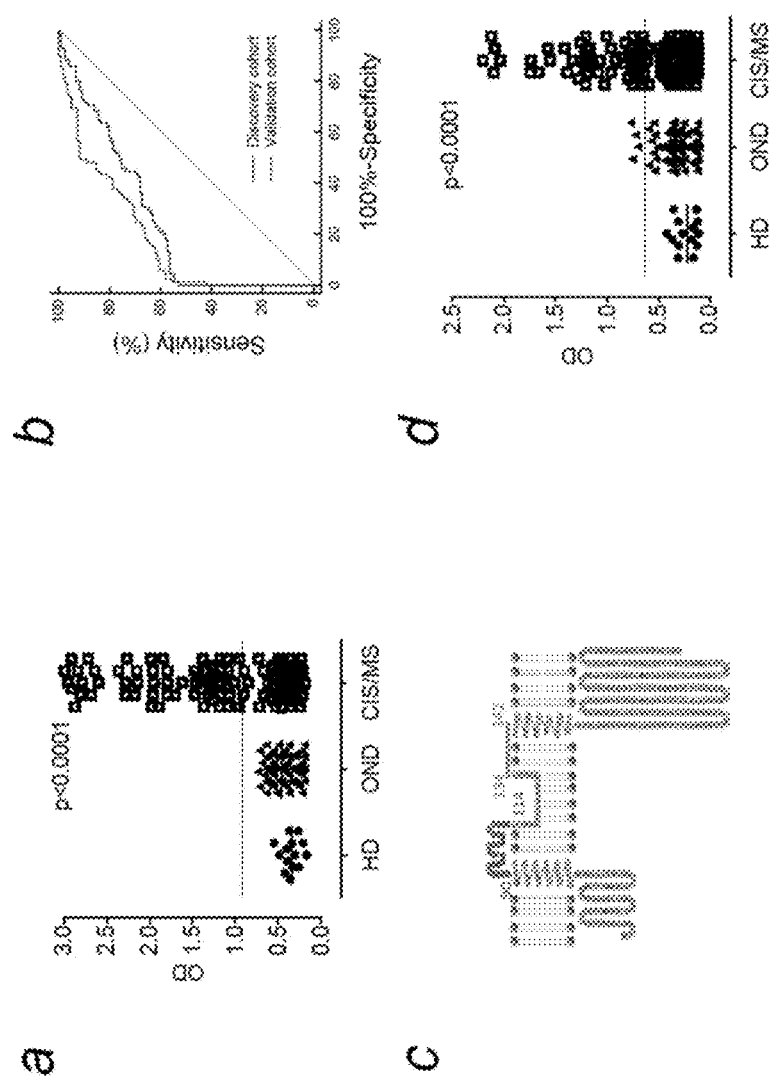

FIG. 4: High titer serum reactivity to KIR4.1 in a subset of MS patients.

(a) Protein based ELISA screening approach for anti-KIR4.1 serum reactivity. Purified recombinant KIR4.1 from HEK293 cells was covalently coupled to the solid phase of ELISA plates. Serum antibody binding to KIR4.1 was determined in HD, OND, and MS patients. The frequency of antibody positive and negative sera were compared between HD (n=14), OND (n=71) and MS patients (n=122) by Kruskal-Wallis test. The threshold for anti-KIR4.1 antibody positivity (cut off OD 0.866, 5 SD above median OD of HD subjects) is indicated by a dashed horizontal line.

(b) ROC curves depicting the diagnostic performance of the anti-KIR4.1 antibody ELISA test in two independent MS and OND patient groups. The discovery cohort (solid line) corresponds to the cohort shown in (a). The validation group (broken line) consisted of 132 OND and 147 MS patients. Area under the ROC curve (AUC), discovery cohort: 0.76 (95% CI: 0.69-0.81), validation cohort: 0.82 (95% CI: 0.76-0.87).

(c) Two dimensional graphical illustration of KIR4.1 protein based on the sequence annotation from uniprot database (http://www.uniprot.org/uniprot/P78508). The large and small extracellular loops are highlighted in red and yellow, respectively.

(d) ELISA assay with plate bound peptide KIR4.183-120 which contains the first extracellular loop of KIR4.1. Serum reactivity against KIR4.183-120 was determined in HD, OND patients, and MS patients of the discovery cohort (see (a)). Antibody positive and negative sera were compared between HD, OND and MS patients by Kruskal-Wallis test. The threshold for anti-KIR4.1 positivity (cut-off OD 0.7558, 5 SD above median OD of HD subjects) is indicated by a broken horizontal line.

Figure 5:
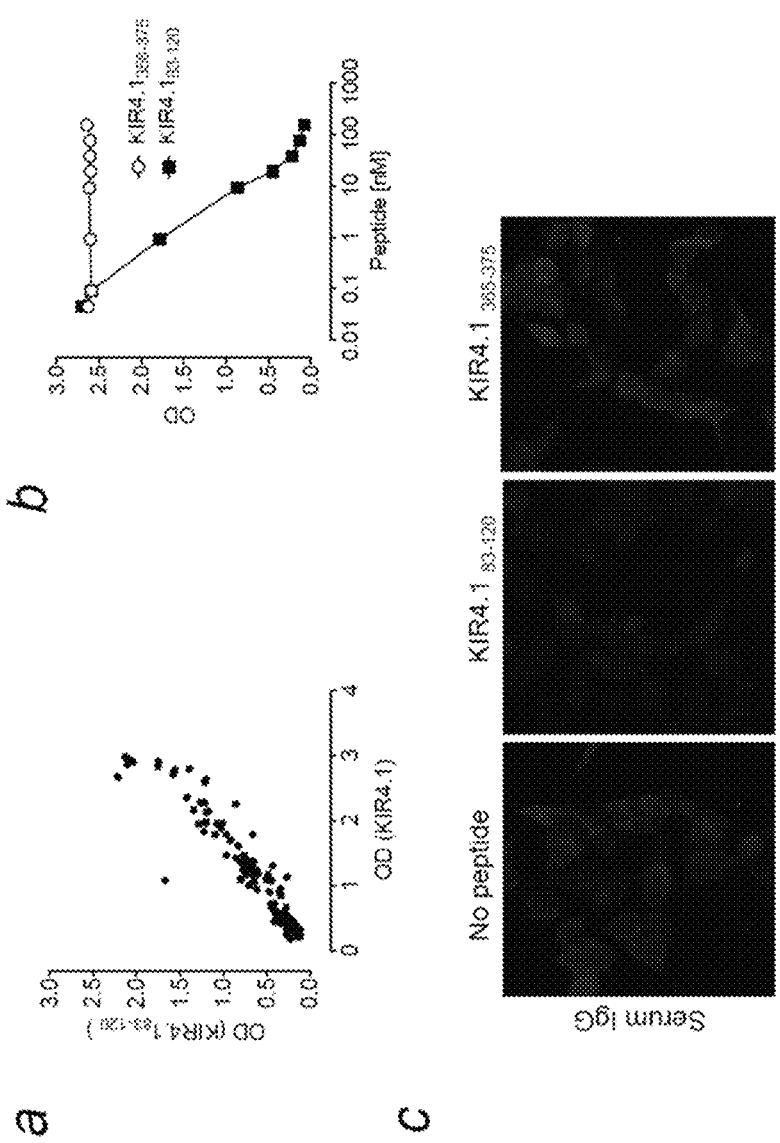

FIG. 5: KIR4.1-specific MS serum IgG antibodies are specific to the extracellular loop or KIR4.1 (KIR4.183-120).

(a) Competitive binding of affinity purified anti-KIR4.1 serum IgG by KIR4.183-120 (first extracellular loop) or KIR4.1356-375 (c-terminal domain) against full length purified recombinant His-tagged KIR4.1. Anti-KIR4.1 serum IgG was immobilized on ELISA plates and incubated with increasing concentrations of peptides (concentration range 0.045-150 nM) in the presence of a fixed concentration (150 nM) of His-tagged recombinant KIR4.1 protein. Binding of KIR4.1 protein was determined by anti-His tag detection antibodies.

(b) Correlation of ELISA assays based on plate bound KIR4.1 protein or KIR4.183-120 peptide for the quantification of anti-KIR4.1 serum reactivity in samples from MS patients (n=122).

(c) Cell based competitive binding assay. HEK293 cells expressing KIR4.1 were immunolabelled with MS serum IgG either without competition (left) or in the presence of KIR4.183-120 (middle) or KIR4.1356-375 (right). Representative microphotographs.

FIG. 6:

(a) Immunofluorescence labeling performed on P10 mouse cerebellar sections. Stainings with MS serum IgG (left panels) and anti-GFAP antibodies (right panels). Scale bar 50 μm.

(b) Perivascular staining pattern obtained with MS serum IgG (left panels) and anti-GFAP antibody immunolabeling (right panels) on human cortical sections. Frames indicate areas of higher power magnification presented in the lower panels. Scale bars 100 μm (upper panels) and 20 μm (lower panels).

Figure 7:
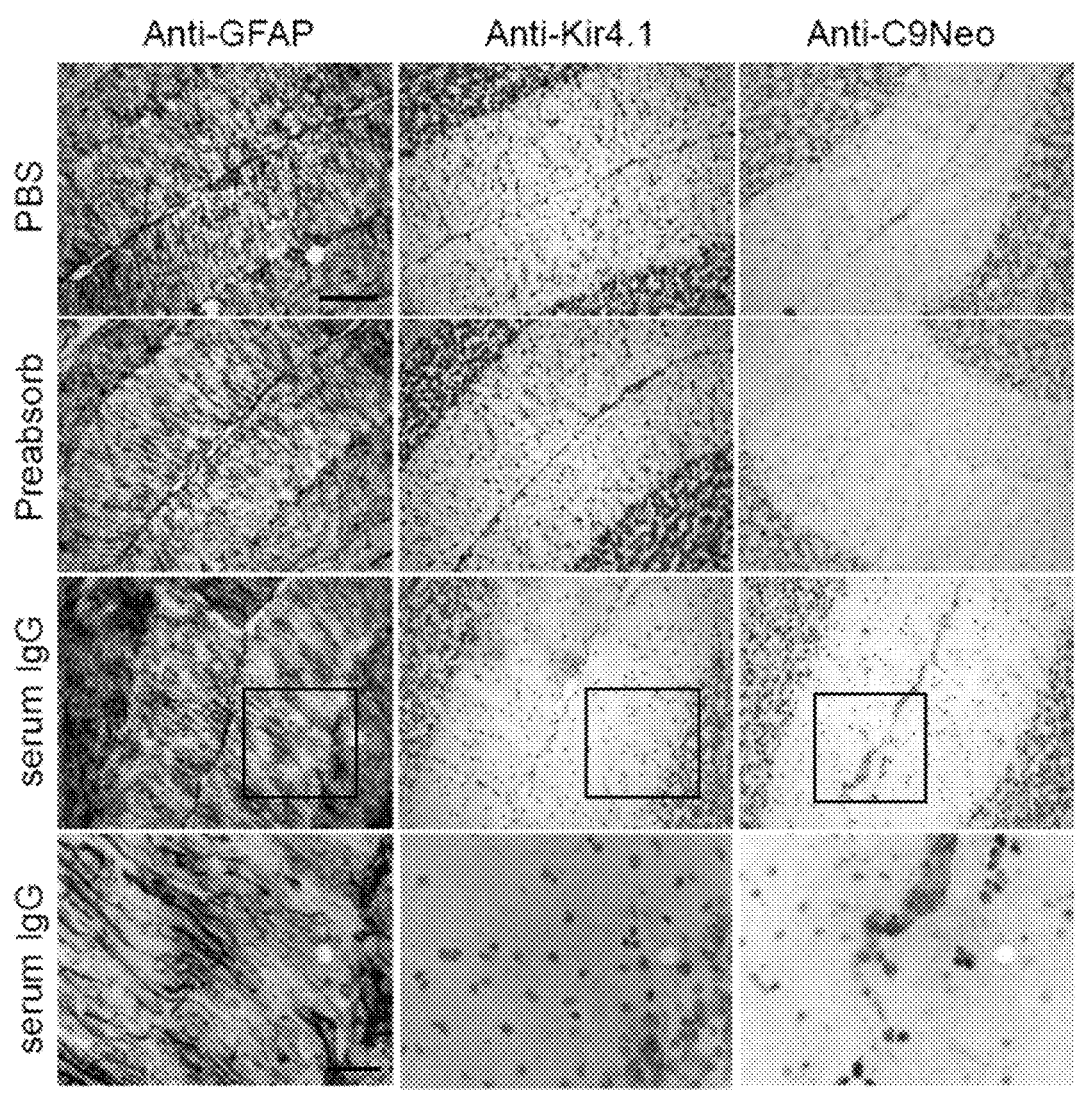

FIG. 7: KIR4.1-specific MS serum IgG antibodies induce loss of KIR4.1 staining, disruption of GFAP filament structures and activation of complement in vivo.

PBS (first row), MS patient serum IgG depleted KIR4.1-specific antibody reactivity (second row), or serum IgG with preserved anti-KIR4.1 reactivity (third and forth row) were injected into the cisterna magna of C57BL/6 mice together with human complement. 24 hrs after injection mice were sacrificed and brain sections were assessed for GFAP (left), KIR4.1 (middle) and C9neo reactivity (right) by immunohistochemistry. Scale bars 50 μm and 20 μm (bottom panels).

FIG. 8:

(a) Purification of His-tagged KIR4.1 protein from HEK293 cells transfected with KIR4.1 expression construct [PcDNA3.1(+)/KIR4.1]. Lane 1: HEK293 cleared lysate; Lane 2: flow-through; Lane 3-5: wash fractions; lane 6-8: elution fractions.

(b) Depletion of anti-KIR4.1 reactivity from the serum IgG of MS patients. Lane 1: beads mixed with mock transfected HEK293 cell lysate and Lane 2: beads mixed with PcDNA3.1 (+)/KIR4.1 transfected HEK293 cell lysate. These beads were used to generate mock preabsorption and preabsorption columns, respectively. Immunoblot on the right shows serum IgG captured by preabsorption column based on bead-bound KIR4.1.

(c) The non-concentrated flow through from mock preabsorption and preabsorption columns was tested for KIR4.1 reactivity by recombinantly purified KIR4.1 ELISA.

EXAMPLES

The examples illustrate the invention:

Example 1

Materials and Methods
Patients and Controls

Patients and controls were recruited at the Department of Neurology, Klinikum rechts der Isar of the Technische Universität in Munich. Two independent cohorts of MS patients, patients with high-risk clinically isolated syndrome were included in the study. Control groups consisted of age matched healthy donors (HD) or patients with other neurological diseases (OND). The characteristics of patients and controls are given in table 1. The ethics committees of the University approved the study.

| Sample characteristics | Discovery cohort | | | Validation cohort | |
|---|---|---|---|---|---|
| | HD (n = 14) | OND† (n = 71) | MS (n = 122) | OND† (n = 130) | MS (n = 149) |
| Age (years) | | | | | |
| Mean | 34 | 48 | 38 | 49 | 36 |
| Range | (25-48) | (16-85) | (18-73) | (21-78) | (18-63) |
| Gender (No.) | | | | | |
| Female:Male | 8:6 | 37:34 | 77:45 | 58:72 | 90:59 |

Abbreviations: HD = healthy donors, OND = other neurological diseases, MS = multiple sclerosis.
†OND include patients with bacterial or viral meningitis, viral encephalitis, neurosyphilis and HIV infection.

Antibodies

Rabbit polyclonal anti-human/mouse/rat KIR4.1 (obtained from Millipore, Billerica, Mass., USA, and Sigma-Aldrich, St. Louis, Mo., USA), mouse monoclonal anti-human/rat KIR4.1 (Sigma-Aldrich), monoclonal anti-rat/mouse GFAP (Invitrogen), rabbit anti-human C9 neo or purified serum IgG were used as primary antibodies and biotin-, AlexaFluor 488-, or AlexaFluor 555-tagged rabbit polyclonal anti-human, anti-rat (Invitrogen, Carlsbad, Calif., USA), or anti-mouse IgG (Vector Laboratories Inc., Burlingame, Calif., USA) were used as secondary antibodies in all immunolabeling experiments.

Immunofluorescence and Immunohistochemistry

For immunofluorescence staining freshly dissected CNS tissue of mouse, rat, or human origin was snap frozen and embedded in tissue-tek O.C.T (VWR Int., LLC, Radnor, Pa., USA). Cryo-sectioning was performed at −20° C. to obtain 10 μm sections. After fixation with 100% ice cold methanol for 10 min, blocking steps were performed with peroxidase, avidin and biotin blocking reagents (Vector Laboratories Inc.) for 15 min each and with 10% goat, mouse or rat serum in PBS-T (0.05% tween-20 in phosphate buffer saline pH 7.0) for 30 min. Sections were then incubated with diluted purified serum IgG (10 μg/ml in PBS-T) or with a commercial antibody solution overnight at 4° C. After multiple washing steps, sections were incubated with biotin-tagged secondary antibodies for 1 hr at room temperature. Section were further incubated with Avidin-biotin complex (Vector) for 1 hr, with 1 ul of biotinylated tyramide in PBS with 8.8 mM of $H_2O_2$. All washing steps were performed with PBS-T. Antibody binding was detected with AlexaFluor 488- or AlexaFluor 555-labeled avidin. Nuclear staining was performed using Gold antifade with DAPI (Invitrogen). After incubation with Avidin-biotin complex, secetion were developed either with DAB chromogen (Dako) or AEC chromogen (Sigma). Counterstaining was done with hemalum solution. In case of DAB chromogen they were dehydrated and mounted with xylene compatible roto-histo kit mounting medium and for AEC with water soluble mounting medium (Vector). Images were taken using a Zeiss Cell Observer microscope with an AxioCam MRm camera (Carl Zeiss MicroImaging, Ltd., Göttingen, Germany).

Preparation of Membrane Protein Enriched CNS Tissue Fraction

CNS tissue from 8 rat brains or human brain (2.4 g) was homogenized using a glass tissue homogenizer in ice cold homogenization buffer (0.32M sucrose, 10 mM HEPES pH 7.4, 2 mM EDTA) and protease inhibitor cocktail (Sigma-Aldrich). The suspension was centrifuged at 1000 g to pellet down the nuclear fraction. High speed centrifugation and sucrose gradient method was used for the enrichment of the membrane fraction. The enriched membrane pellet was resuspended in HEPES lysis buffer (50 mM HEPES pH 7.4, 2 mM EDTA, and protease inhibitor cocktail). The enriched membrane fraction from CNS tissue was used to prepare a cyanogen bromide (CNBr) activated sepharose bead-based enrichment column (GE Healthcare Life Sciences, Pittsburgh, Pa., USA) according to the manufacturer's protocol.

Immunoprecipitation, 2-D Electrophoresis and Western Blotting

CNS membrane reactive serum IgG antibodies from 12 MS patients were enriched using CNBr activated sepharose enrichment column (see above) and were purified using a protein G bead-based approach (GE Healthcare Life Sciences). The purified MS serum IgG antibodies were pooled together and used for immunoprecipitation of reactive antigens with magnetic protein G beads (Invitrogen) based purification columns according to the manufacturer's protocol. The eluted antigen fractions were precipitated with chloroform-methanol and were solublized with a 2-D protein solubilizer (Invitrogen). The solublized fractions were loaded on iso-electric focusing strips (Invitrogen) and run at pH 3-10 or pH 4-6. To identify the immunoprecipitated CNS antigens, 2-D-electrophoresis was performed with small 2-D benchtop technology (Invitrogen). Spots were removed and subjected to matrix-assisted laser desorption/tandem mass spectrometry (MALDI-MS/MS; Alphalyse, Inc., CA, USA) for identification. As control, we ran parallel samples involving pooled serum IgG antibodies purified from 24 OND patients.

For validation, rat kidney lysate (RKL)[41], human brain lysate (HBL) and in vitro translated KIR4.1 protein were subjected to immunoprecipitation with serum IgG from MS patients and controls using a protein G sepharose beads (Invitrogen). A total of 4 mg purified serum IgG diluted in 5 ml PBS was captured on 400 μl bead suspension and cross linked by dimethyl pimelimidate (DMP)-2HCl in 50 mM borate buffer at room temperature (RT). After cross linking, excess DMP was quenched with 50 mM borate buffer and blocking was performed with ethanolamine buffer (200 mM, pH 8.0). Prepared beads were used to immunoprecipitate KIR4.1 from RKL HBL and KIR4.1 in vitro translation reaction mix. All western blotting experiments were performed on 4-12% SDS gels (Invitrogen) with rabbit polyclonal anti-human KIR4.1 antibody using ECL detection system (GE Healthcare Life Sciences).

In vitro-translation of KIR4.1 Protein

Human brain total RNA was used to synthesize full-length cDNA encoding KIR4.1. The primers 5' GGA TCC ATG ACG TCA GTT GCC AAG GTG 3' and 3' CTC GAG TCA GAC ATT GCT GAT GCG CAC 5' were used to add the restriction sites BamH1 and Xho1 at the 5' and 3' ends, respectively. The PCR product was cloned into the plasmid pT7CFE1-CHIS (Pierce, Thermo Fisher Scientific, Rockford, Ill., USA). In-vitro translation was performed with human protein expression kit (Pierce, Thermo Fisher Scientific) according to the manufacturer's protocol. A pT7CFE1-CHIS construct encoding green fluorescence protein (GFP) was used as control in all in-vitro translation experiments. Western blotting was performed on 4-12% SDS gel (Invitrogen) to confirm the KIR4.1 expression using a rabbit polyclonal anti-human KIR4.1 antibody with ECL detection.

Preparation of Murine Primary Cortical Astroglial Culture and Flow Cytometry

For the isolation of primary cortical astroglial cells mouse pups were sacrificed, and cerebellum and optic nerve were dissected and placed in ice cold buffer [1.47 M Nacl, 5 mM Kcl, 0.2 mM NaHPO4(2H2O), 0.2 mMKH2PO4, 5.5 mM glucose, 0.058 M sucrose in 1 liter, ph6.5]. The tissue was minced and digested with 0.5% trypsin at 37° C. for 10 min, subsequently. After washing with MG medium [MEM medium (Sigma-Aldrich) supplemented with 10% FCS (low endotoxin), 1% L-glutamine, and 0.5% Pen/Strep], a pasteur pipette with a melted tip was used to generate tissue suspensions. For astroglial culture, the tissue suspension was seeded in MG medium. Fresh medium was provided after every two to three days. After two weeks, the mixed glial cell culture obtained was subjected to gentle shaking at 37° C. for 6 hrs to remove microglia. The astroglial culture was used in double immuoflourescence staining experiments and flow cytometric analyses (CyAn ADP, Beckmann Coulter Inc., FL) using serum IgG antibodies from MS and OND patients and anti-mouse GFAP as primary antibodies.

Cloning, Expression and Purification

For recombinant KIR4.1 expression in HEK293 cells, a full length cDNA encoding human KIR4.1 with C-terminal hexa-histidine tag (his-tag) was synthesized from total human brain mRNA (BD Biosciences, San Jose, Calif.) using 5"-GCG GCC GCA CCA TGA CGT CAG TTG CCA AGG TGT ATT ACA GTC AG-3" and 5"-CTC GAG TCA GTG GTG GTG GTG GTG GTG GAC ATT GCT GAT GCG CAC-3' as forward and reverse primers (his-tag encoding sequence is underlined). Cloning into pcDNA 3.1(+) (Invitrogen) was carried out using NotI and XhoI restriction sites inserted via forward and reverse primers respectively to obtain pcDNA 3.1(+)/KIR4.1 expression construct. HEK 293 cells were transiently transfected with pcDNA 3.1(+)/KIR4.1 using lipofectamine 2000 transfection reagent (Invitrogen) according to the manufacturer's instructions. At 6 hr post-transfection medium was supplemented with 10% FCS and 300 mM barium chloride. At 36 hours post-transfection cells were harvested and washed twice with ice cold PBS. After counting 30 million cells were subjected to lysis in 10 ml of 50 mM sodium phosphate buffer pH 7.4 containing 550 mM sodium chloride, 5 mM Tris-HCl, 1.0% Fos-Choline, 500 unit of Benzonase® nuclease (Sigma) and 1×EDTA free protease inhibitor cocktail (Sigma). Cell lysate was centrifuged at 20,000 rpm, using SS34 rotor on Sorvall RC6 plus centrifuge for 30 minutes at 4° C. After centrifugation supernatant (cleared lysate) was collected and a total of 40 mg protein was loaded onto a purification column containing 1 ml of His-Pure™ cobalt resin (Pierce) pre-equilibrated with 5 ml of binding buffer (same as lysis buffer). Washing was carried out with 6 ml of washing buffer (same as lysis buffer). Elution of his-tagged protein fraction was carried out with 3 ml elution buffer (50 mM sodium phosphate, 300 mM sodium chloride, 150 mM imidazole; pH 6.0). Finally, the elution fraction was dialyzed against PBS and tested for the presence of purified KIR4.1 by western blot analysis probing with rabbit anti human 4.1 antibody (Millipore).

Enzyme Linked Immunosorbent Assays (ELISA)

For the detection of serum reactivity in MS and control patients with CNS membrane proteins, rat cerebellum (400 mg snap frozen) was used to prepare protein fractions enriched for membrane and cytoplasmic antigens. Protein fractions were surface biotinylated with Sulfo-NHS-SS-Biotin (Pierce) and were diluted in PBS to final concentration of 80 µg/ml. For coating 100 µl of diluted protein fraction was added to each well of Nunc Immobilizer™ streptavidin pre-coated and pre-blocked ELISA plates (Pierce). Plates were left overnight 4° C. on a rotary shaker with slight shaking. After coating plates were washed twice with PBS-T.

For screening of anti-KIR4.1 reactivity in serum samples solid phase bound purified recombinant KIR4.1 was used. Purified KIR4.1 protein was diluted in PBS to a final concentration of 6 µg/ml and 100 µl were added to each well of Nunc Immobilizer™ amino plates (Pierce). Plates were left overnight 4° C. on a rotary shaker with slight shaking. Coated plates were washed twice with PBS-T and blocked for 1 hr using 10 mM ethanolamine in 100 mM Na-Carbonate pH 9.6.

For screening of anti-KIR4.1 extracellular peptide reactivity in serum samples, the amino acid sequence representing the first and second extracellular loops of KIR4.1 protein [GVVWYLVAVAHGDLLELDPPANHTPCV-VQVHTLTGAFL (large extracellular domain; $KIR4.1_{83-120}$; SEQ ID: NO: 1; underlined sequence: $KIR4_{90-114}$; SEQ ID NO: 4) and TIGYGFRYISEECPLAIVLLI (small extracellular domain; $KIR4.1_{128-148}$; SEQ ID NO: 2; underlined sequence: $KIR4.1_{134-142}$; SEQ ID NO: 5) respectively] with N-terminal biotin modification were purchased from JPT peptide Technologies Ltd. (Berlin, Germany). The peptides were diluted at 16 µg/ml in sodium phosphate buffer pH 8.0. Coating was performed on Nunc Immobilizer™ streptavidin pre-coated and pre-blocked ELISA plates (Pierce) as described above. Control ELISA plates were coated with bovine serum albumin (Sigma) in all screening experiments. Serum samples were diluted in 3% skimmed milk (Biorad Inc.) to obtain IgG concentration of 10 µg/ml. An HRP-conjugated anti-human IgG antibody (Dako) was used for detection. The optical density (OD) measurements were carried out at 450 nm on a Tecan microplate reader (Tecan Group Ltd., Switzerland).

Competitive-binding Assay

Total serum IgG was purified by protein G sepharose beads (GE biosciences) according to manufacturer's protocol. For the isolation of KIR4.1 reactive IgG fraction from total serum IgG KIR4.1-bound CNBr activated sepharose affinity beads (GE biosciences) were used. The binding capacity of the isolated KIR4.1 reactive serum IgG fraction was estimated by direct ELISA with purified recombinant KIR4.1. For competitive-binding assays, the KIR4.1 reactive serum IgG was diluted to 5 µg/ml in PBS and added to each well of Nunc Immoblizer™ amino strips (Pierce). Coating and blocking was performed as described. Increasing concentration (12 nM to 144 nM) of extracellular KIR4.1 peptide ($KIR4.1_{128-148}$) or KIR4.1 intracellular C-terminal peptide ($KIR4.1_{356-375}$) was then added to the wells. After 1 hr incubation plates were washed 3 times with PBS-T and 145 nM purified recombinant his-tagged KIR4.1 protein was added to each well for 1 hr. After washing (3 times with PBS-T, an HRP conjugated anti-his tag antibody was used for detection. The competitive-binding assay was performed in duplicates and the performance of the assay was validated with binding of a commercially available anti-KIR4.1 monoclonal antibody (Millipore) to the C-terminal KIR4.1 peptide ($KIR4.1_{356-375}$). The cell based competitive-binding assay was performed on KIR4.1 transfected HEK293 cells using KIR4.1 reactive serum IgG with and without pre-incubation with the extracellular ($KIR_{128-148}$) and intracellular C-terminal ($KIR_{356-375}$) peptides, respectively.

Intrathecal Injection of MS Serum IgG in Mice

MS serum total IgG, MS serum IgG depleted of KIR4.1 reactivity and PBS (control) injection aliquots were prepared. For depletion of KIR4.1 reactivity in MS serum IgG KIR4.1- bound Ni-NTA agarose beads (Pierce) were used following the manufacturer's instructions. To prepare injection aliquots all serum IgG preparations were concentrated to 30 mg/ml using a 10 kD cutoff spin concentrator (Pierce). Twenty microlitre injection aliquot containing equal volume of concentrated serum IgG (or PBS) and human total complement (30 units/ml) were prepared. Six to eight-week-old C57BL/6 mice were divided into 3 groups (n=3-6 mice) each receiving either MS serum total IgG with or without depletion of KIR4.1 reactivity or PBS. Mice were anaesthetized by isoflurane inhalation. A transcutaneous intracisternal injection protocol was adapted as previously described (Klein M, Ann Neurol. 2003, October; 54(4):451-8). After 24 hrs the mice were sacrificed followed by perfusion with ice-cold PBS and paraformaldehyde (4%, pH 7.4) through the left cardiac ventricle. Brainstem and cerebellum were dissected and placed in 20% sucrose at 4° C. overnight. Sagittal pieces of brainstem and cerebellum were embedded in Tissue Tek (Sakura), frozen in liquid nitrogen and cryotomized at 10 µm (Leica CM3050S). Immunohistochemistry was performed as described.

Statistical Analysis

Sera were considered antibody positive when the OD exceeded the cut-off value determined by titers observed in HD [median OD plus 5 times standard deviation]. The Kruskal-Wallis test was used to compare the number of antibody positive and negative patients in the OND and MS group. A p-value below 0.05 was considered significant. Receiver operating characteristic (ROC) analysis was performed and the areas under ROC curves (AUC) were computed for two independent sets of samples using MedCalc (or Analyse-it) software.

Example 2

MS Serum IgG Antibodies Specifically Bind Membrane Antigens in the CNS

Figure 1:
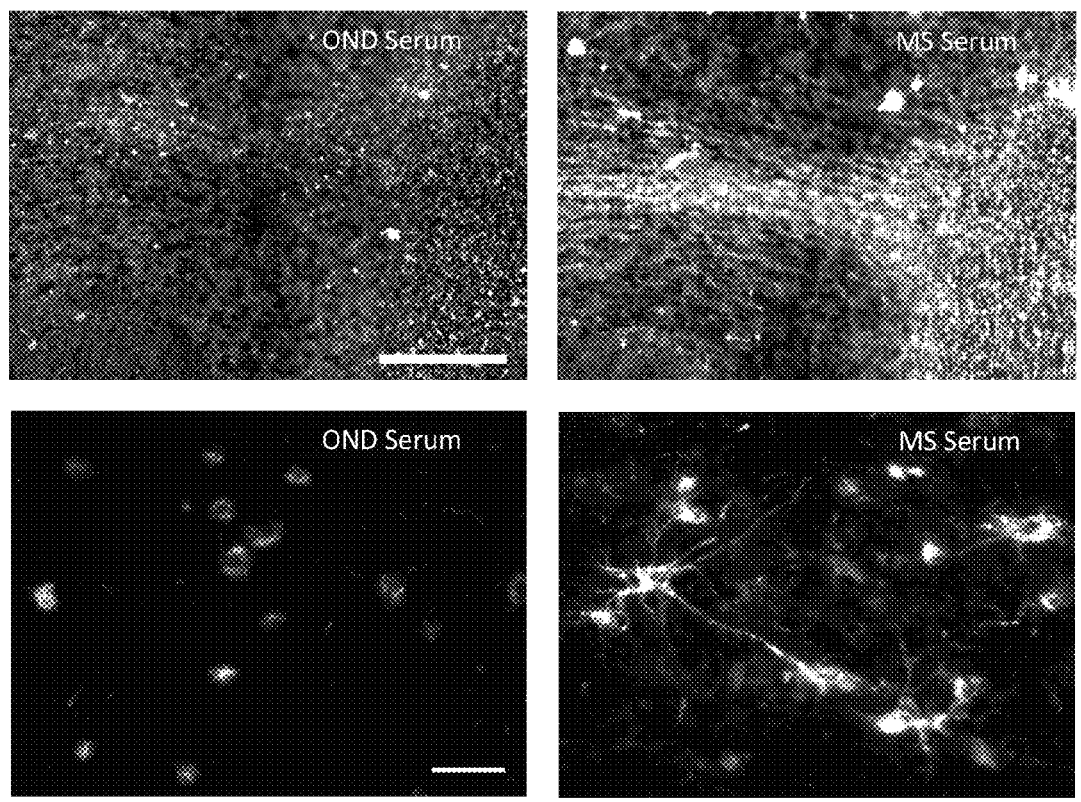
FIG. 1: MS Serum IgG reactivity with CNS membrane antigens (a) Representative photomicrographs of immunofluorescence labeling performed on rat cerebellar (upper panels) and human brain sections (lower panels) with serum IgG from patients with MS or OND patients as indicated. Scale bars 100 µm (upper panels) and 20 µm (lower panels).
Figure 1:
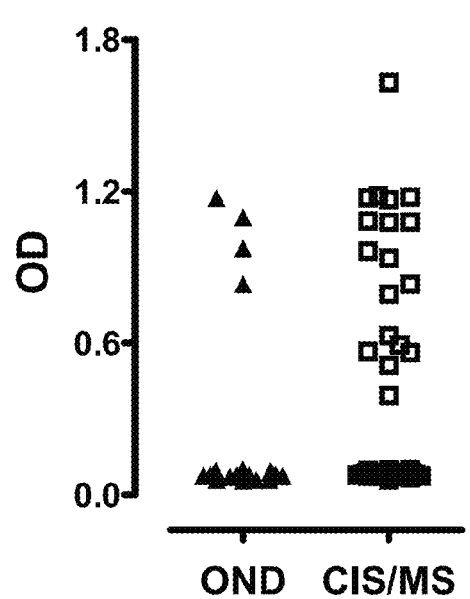

IgG antibodies were purified from serum samples of 19 MS patients and 24 patients with other neurological diseases (OND) and tested for their reactivity with rat and human brain tissue sections by immunofluorescence. Using MS serum IgG, we observed a membrane immunoreactivity in 37% (7/19) on rat cerebellar and in 58% (11/19) on human brain sections (FIG. 1a). In contrast, we could not find this particular staining pattern using serum IgG from any of the OND patients (FIG. 1a). To confirm the specific membrane reactivity, we established a capture ELISA based on rat cerebellar protein fractions enriched for membrane and cytoplasmic antigens. An elevated reactivity with membrane protein fraction was only observed in sera from MS patients (n=56) but not in sera from OND patients (n=29) suggesting the presence of a specific serum IgG antibody against a CNS membrane protein in MS patients (FIG. 1b). In comparison, reactivity to the cytoplasmic protein fraction was similar in both sera from MS and OND patients (data not shown). Thus, in the subsequent immunoprecipitation studies we proceeded with the CNS tissue fraction enriched for membrane proteins for the identification of target antigens in MS.

Example 3

Identification of KIR4.1 as the Target of Serum IgG in MS

The CNS reactive serum IgG from 12 MS patients were pooled and enriched using CNBr activated beads coated with membrane protein fraction prepared from human brain tissue. The MS serum IgG eluted from the enrichment column was used for subsequent antigen immunoprecipitation. The antigen-IgG complexes eluted from the precipitation column were then analyzed on SDS-PAGE and separated by 2-D gel electrophoresis (FIG. 2a). 7 protein spots were excised and analyzed by MALDI-MS/MS, the abbreviation "MS" referring to mass spectrometry in this specific context. In one of the spots the inward rectifying potassium channel KIR4.1 was identified. The identity of KIR4.1 as MS serum IgG antibody target was subsequently confirmed by immunoprecipitation and Western blotting using extracts from rat kidney lysate, human brain lysate (FIG. 2b), and in vitro translated KIR4.1 reaction mix (FIG. 2c).

Example 4

Figure 6:
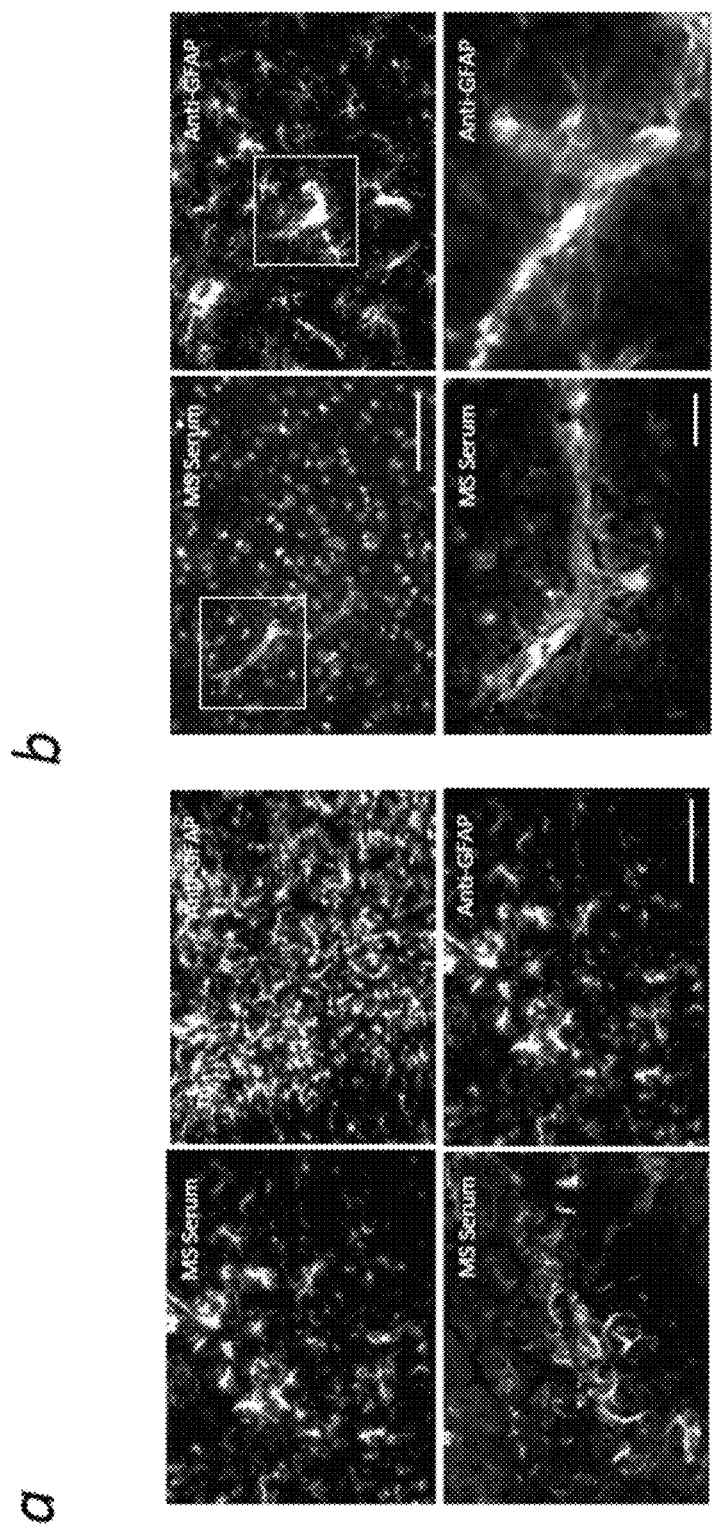

KIR4.1 Reactivity with MS Serum IgG Localizes to Hippocampal and Cerebellar Astroglia Double immunofluorescence labeling was performed on rat brain sections with both purified IgG antibodies from MS sera and the anti-KIR4.1 monoclonal antibody (FIG. 3a). As control, a similar staining was performed with purified IgG from sera of OND patients. Specific co-localization of the monoclonal anti-KIR4.1 and the serum IgG antibody on rat cerebellar sections was only observed for MS-IgG but not for OND-IgG (FIG. 3a). To further validate this observation we performed immunolabeling of cerebellar sections from 10 day-old wildtype and Kir4.1 null mice (Kir4.1$^{-/-}$) mice with MS serum IgG (FIG. 3b). On day 10 after birth (P10), KIR4.1 is known to be expressed in high amounts (20). KIR4.1 antibody positive MS sera stained astroglial cells in cerebellar and hippocampal sections of wild type mice but failed to react with sections from Kir4.1$^{-/-}$ mice (FIGS. 3b and FIG. 6). KIR4.1 antibody negative sera did not stain CNS tissue from either wildtype mice or Kir4.1$^{-/-}$ mice (data not shown). To confirm the astroglial localization of the anti-KIR4.1 reactivity in MS sera, we prepared murine mixed glial primary cultures. A highly MS serum-specific membrane staining was observed in GFAP-positive cells (FIG. 3c). A similar MS serum-specific surface staining of glial cells was also observed by flow cytometry (FIG. 3d).

Example 5

High Titer Serum Reactivity to the Extracellular Loop of KIR4.1 Protein is Restricted to MS For the quantification of anti-KIR4.1 reactivity we used a capture ELISA assay based on KIR4.1 protein isolated from the human PC3 cell line. Sera from 122 MS/CIS, 70 OND patients and 14 healthy donors (HD) were analysed (FIG. 4a). Significant KIR4.1 serum autoantibody concentrations (>5 SD from median of healthy controls) were detected in 16.9% of OND patients (12/71) and 50.8% of MS patients (62/122) (p<0.0001). All positive MS sera contained higher antibody concentrations than any serum of the OND group.

These findings were independently confirmed in second case-control cohort involving 130 OND and 149 MS patients (FIG. 4d).

Similar results were obtained in a smaller, group of patients and controls by an ELISA assay in which in vitro translated KIR4.1 protein was used as capture substrate (data not shown). None of the sera from OND patients contained significantly elevated antibody titers, whereas 22.5% (10/44) of MS patient sera were antibody positive (p=0.0108) in this assay.

Membrane topology analysis (Uniprot database version 107, entry 78508 (last modified Apr. 5, 2011); http://www.uniprot.org/uniprot/P78508) predicts two extracellular loops for the KIR4.1 protein; a larger loop spanning 25 amino acids (KIR4.190-114; SEQ ID NO: 4) and a smaller loop spanning 9 amino acids (KIR4.1134-142; SEQ ID NO: 5); see FIG. 4c.

To mimic the external loop topology of KIR4.1, peptides comprising the amino acid sequence of the extracellular regions of KIR4.1 and the adjacent intramembrane domains were synthesized with biotin tags and immobilized on avidin coated plates. Sera from MS patients and controls were tested for antibody binding to these peptides. Antibody reactivity to the peptide representing the smaller extracellular domain of KIR4.1 (KIR4.1128-148; SEQ ID NO: 2) was observed in only 4% of the MS patients and in no HD or OND patients (data not shown). However, when MS sera were assayed for their binding capability to the first extracellular loop of KIR4.1 (KIR4.183-120; SEQ ID NO: 1), significantly elevated antibody concentrations were observed in MS patients (37/122, 30.3%) versus OND patients (1/70, 1.4%) ($p<0.0001$). This observation was independently replicated in a second case-control cohort (data not shown).

Binding of human KIR4.1-specific antibodies to the large extracellular domain was further confirmed in a competition assay; see FIG. 5.

Overall, we observed a strong correlation between the antibody reactivity measured by the KIR4.1 protein based ELISA from PC3 cells and the KIR4.183-120 peptide (SEQ ID NO: 1) based ELISA assays suggesting that the MS serum antibodies against KIR4.1 recognize an epitope in the first extracellular loop of KIR4.1.

Example 6

Figure 8:
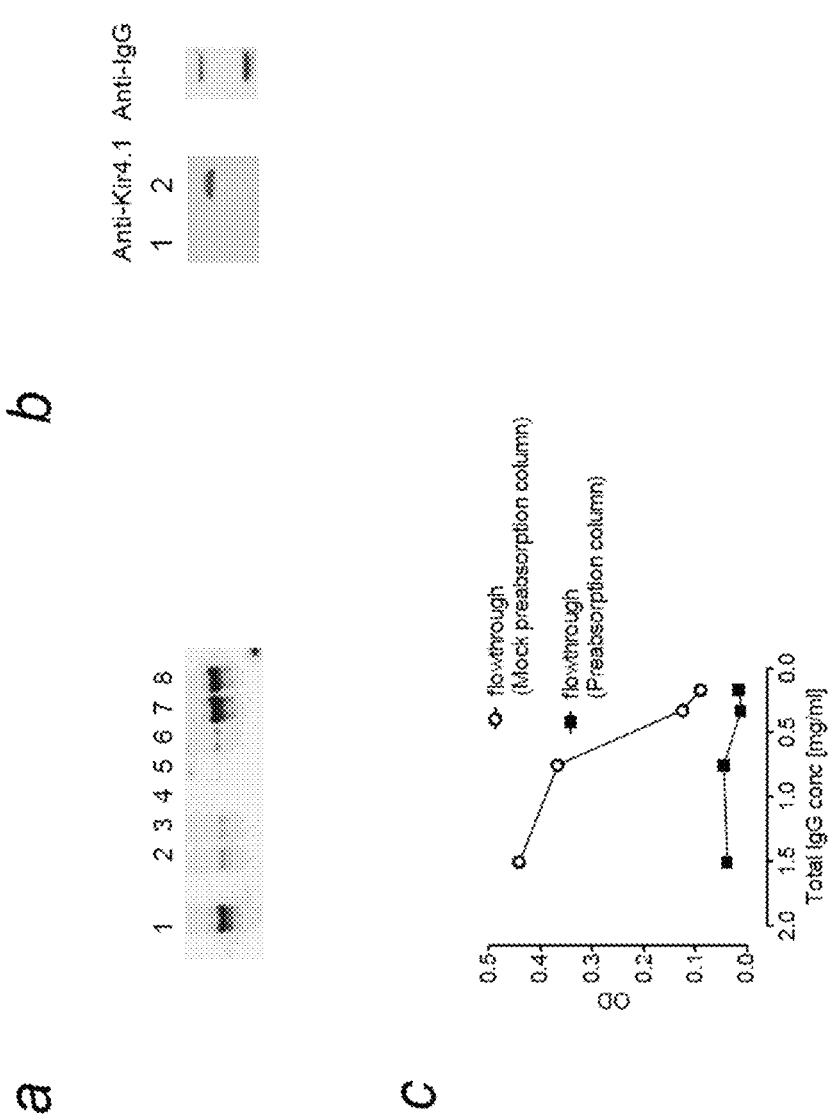

Serum KIR4.1-Specific Antibodies Induce Loss of KIR4.1 Expression, Disruption of GFAP Filament Structures and Activation of Complement In Vivo Mice injected with serum IgG containing KIR4.1-specific antibodies showed disruption of the GFAP filament structures in astrocytes, loss of KIR4.1 expression and activation of complement in areas where KIR4.1 loss was observed. These changes were not observed in mice which received PBS or the serum IgG from the same patient, which was depleted from KIR4.1-specific antibodies. Corresponding data are displayed in FIGS. 7 and 8.

FURTHER REFERENCES

1. J. H. Noseworthy, C. Lucchinetti, M. Rodriguez, B. G. Weinshenker, Multiple sclerosis. *N. Engl. J. Med.* 343, 938-952 (2000).
2. A. Ascherio, K. L. Munger, Environmental risk factors for multiple sclerosis. Part II: Noninfectious factors. *Ann. Neurol.* 61, 504-513 (2007).
3. A. Ascherio, K. L. Munger, Environmental risk factors for multiple sclerosis. Part I: the role of infection. *Ann. Neurol.* 61, 288-299 (2007).
4. D. A. Hafler, A. Compston, S. Sawcer, E. S. Lander, M. J. Daly, P. L. de Jager, P. I. de Bakker, S. B. Gabriel, D. B. Mirel, A. J. Ivinson, M. A. Pericak-Vance, S. G. Gregory, J. D. Rioux, J. L. McCauley, J. L. Haines, L. F. Barcellos, B. Cree, J. R. Oksenberg, S. L. Hauser, Risk alleles for multiple sclerosis identified by a genomewide study. *N. Engl. J. Med.* 357, 851-862 (2007).
5. H. F. McFarland, R. Martin, Multiple sclerosis: a complicated picture of autoimmunity. *Nat. Immunol.* 8, 913-919 (2007).
6. B. Hemmer, J. J. Archelos, H. P. Hartung, New concepts in the immunopathogenesis of multiple sclerosis. *Nat. Rev. Neurosci.* 3, 291-301 (2002).
7. M. K. Storch, S. Piddlesden, M. Haltia, M. Iivanainen, P. Morgan, H. Lassmann, Multiple sclerosis: in situ evidence for antibody- and complement-mediated demyelination. *Ann. Neurol.* 43, 465-471 (1998).
8. C. Lucchinetti, W. Bruck, J. Parisi, B. Scheithauer, M. Rodriguez, H. Lassmann, Heterogeneity of multiple sclerosis lesions: implications for the pathogenesis of demyelination. *Ann. Neurol.* 47, 707-717 (2000).
9. M. Keegan, F. Konig, R. McClelland, W. Bruck, Y. Morales, A. Bitsch, H. Panitch, H. Lassmann, B. Weinshenker, M. Rodriguez, J. Parisi, C. F. Lucchinetti, Relation between humoral pathological changes in multiple sclerosis and response to therapeutic plasma exchange. *Lancet* 366, 579-582 (2005).
10. S. L. Hauser, E. Waubant, D. L. Arnold, T. Vollmer, J. Antel, R. J. Fox, A. Bar-Or, M. Panzara, N. Sarkar, S. Agarwal, A. Langer-Gould, C. H. Smith, B-cell depletion with rituximab in relapsing-remitting multiple sclerosis. *N. Engl. J. Med.* 358, 676-688 (2008).
11. A. Uccelli, F. Aloisi, V. Pistoia, Unveiling the enigma of the CNS as a B-cell fostering environment. *Trends Immunol.* 26, 254-259 (2005).
12. E. Meinl, M. Krumbholz, R. Hohlfeld, B lineage cells in the inflammatory central nervous system environment: migration, maintenance, local antibody production, and therapeutic modulation. *Ann. Neurol.* 59, 880-892 (2006).
13. F. J. Quintana, M. F. Farez, V. Viglietta, A. H. Iglesias, Y. Merbl, G. Izquierdo, M. Lucas, A. S. Basso, S. J. Khoury, C. F. Lucchinetti, I. R. Cohen, H. L. Weiner, Antigen microarrays identify unique serum autoantibody signatures in clinical and pathologic subtypes of multiple sclerosis. *Proc. Natl. Acad. Sci. U.S. A* 105, 18889-18894 (2008).
14. I. Cortese, R. Tafi, L. M. Grimaldi, G. Martino, A. Nicosia, R. Cortese, Identification of peptides specific for cerebrospinal fluid antibodies in multiple sclerosis by using phage libraries. *Proc. Natl. Acad. Sci. U.S. A* 93, 11063-11067 (1996).
15. J. J. Archelos, J. Trotter, S. Previtali, B. Weissbrich, K. V. Toyka, H. P. Hartung, Isolation and characterization of an oligodendrocyte precursor-derived B-cell epitope in multiple sclerosis. *Ann. Neurol.* 43, 15-24 (1998).
16. S. Cepok, D. Zhou, R. Srivastava, S. Nessler, S. Stei, K. Bussow, N. Sommer, B. Hemmer, Identification of Epstein-Barr virus proteins as putative targets of the immune response in multiple sclerosis. *J. Clin. Invest* 115, 1352-1360 (2005).
17. V. Somers, C. Govarts, K. Somers, R. Hupperts, R. Medaer, P. Stinissen, Autoantibody profiling in multiple sclerosis reveals novel antigenic candidates. *J. Immunol.* 180, 3957-3963 (2008).
18. T. Berger, M. Reindl, Multiple sclerosis: disease biomarkers as indicated by pathophysiology. *J. Neurol. Sci.* 259, 21-26 (2007).
19. T. Derfuss, C. Linington, R. Hohlfeld, E. Meinl, Axo-glial antigens as targets in multiple sclerosis: implications for axonal and grey matter injury. *J. Mol. Med.* 88, 753-761 (2010).
20. Y. V. Kucheryavykh, L. Y. Kucheryavykh, C. G. Nichols, H. M. Maldonado, K. Baksi, A. Reichenbach, S. N. Skatchkov, M. J. Eaton, Downregulation of Kir4.1 inward rectifying potassium channel subunits by RNAi impairs potassium transfer and glutamate uptake by cultured cortical astrocytes. *Glia* 55, 274-281 (2007).
21. E. A. Nagelhus, Y. Horio, A. Inanobe, A. Fujita, F. M. Haug, S. Nielsen, Y. Kurachi, O. P. Ottersen, Immunogold evidence suggests that coupling of K+ siphoning and water transport in rat retinal Muller cells is mediated by a coenrichment of Kir4.1 and AQP4 in specific membrane domains. *Glia* 26, 47-54 (1999).
22. M. Amiry-Moghaddam, A. Williamson, M. Palomba, T. Eid, N. C. de Lanerolle, E. A. Nagelhus, M. E. Adams, S. C. Froehner, P. Agre, O. P. Ottersen, Delayed K+ clearance associated with aquaporin-4 mislocalization: phenotypic defects in brains of alpha-syntrophin-null mice. *Proc. Natl. Acad. Sci. U.S.A* 100, 13615-13620 (2003).

The invention claimed is:

1. A method for diagnosing multiple sclerosis or a predisposition for multiple sclerosis in a subject, the method comprising
   Contacting a sample obtained from said subject containing an anti-KIR4.1 antibody with a receptor specific for said anti-KIR4.1 antibody; and
   (b) detecting the formation of a receptor-anti-KIR4.1 antibody complex, wherein said receptor is selected from the group consisting of SEQ ID NO:1, SEQ ID NO:2, KIR 4.1 protein SEQ ID NO:3, SEQ ID NO:4, SEQ ID NO:5, and an antibody binding to said anti-KIR4.1 antibody,
   wherein the presence of an anti-KIR4.1 antibody in said sample is indicative of multiple sclerosis or a predisposition for multiple sclerosis.

2. The method of claim 1, wherein, in case an anti-KIR4.1 antibody is present in said sample,
   (i) presence of at least one clinical symptom of multiple sclerosis in said subject is indicative of multiple sclerosis; and
   (ii) absence of any clinical symptom of multiple sclerosis is indicative of said predisposition for multiple sclerosis.

3. The method of claim 1, wherein said subject has clinically isolated syndrome (CIS).

4. The method of claim 1, wherein the anti-KIR4.1 antibody binds to KIR4.1 (SEQ ID NO: 3) or an extracellular domain thereof, said extracellular domain consisting of the sequence set forth in any one SEQ ID NOs: 1, 2, 4 or 5.

5. A method of screening for a drug or lead compound, said method comprising:
   bringing a test compound into contact with a complex comprising
   (i) an anti-KIR4.1 antibody; and
   (ii) a receptor selected from the group consisting of SEQ ID NO:1, SEQ ID NO:2, SEQ ID NO:3, SEQ ID NO:4, SEQ ID NO:5, and an antibody binding to said anti-KIR4.1 antibody,
   wherein a reduction of the amount of said complex is indicative of the test compound being a drug or lead compound.

6. An ex vivo method of removing anti-KIR4.1 antibodies from blood or serum or reducing the amount thereof, said method comprising
   (a) bringing blood removed from a subject into contact with a receptor selected from the group consisting of SEQ ID NO:1, SEQ ID NO:2, SEQ ID NO:3 (KIR 4.1 protein), SEQ ID NO:4, SEQ ID NO:5, and an antibody binding to said anti-KIR4.1 antibody ; and
   (b) performing plasmapheresis.

7. The method of claim 2, wherein at least one clinical symptom is clinically isolated syndrome (CIS).

8. The method of claim 5, wherein the anti-KIR4.1 antibody binds to KIR4.1 (SEQ ID NO: 3) or an extracellular domain thereof, said extracellular domain consisting of the sequence set forth in any one SEQ ID NOs: 1, 2, 4 or 5.

* * * * *

```
                            SEQUENCE LISTING

<160> NUMBER OF SEQ ID NOS: 9

<210> SEQ ID NO 1
<211> LENGTH: 38
<212> TYPE: PRT
<213> ORGANISM: homo sapiens

<400> SEQUENCE: 1

Gly Val Val Trp Tyr Leu Val Ala Val Ala His Gly Asp Leu Leu Glu
1               5                   10                  15

Leu Asp Pro Pro Ala Asn His Thr Pro Cys Val Val Gln Val His Thr
            20                  25                  30

Leu Thr Gly Ala Phe Leu
        35

<210> SEQ ID NO 2
<211> LENGTH: 21
<212> TYPE: PRT
<213> ORGANISM: homo sapiens

<400> SEQUENCE: 2

Thr Ile Gly Tyr Gly Phe Arg Tyr Ile Ser Glu Glu Cys Pro Leu Ala
1               5                   10                  15

Ile Val Leu Leu Ile
            20

<210> SEQ ID NO 3
<211> LENGTH: 379
<212> TYPE: PRT
<213> ORGANISM: homo sapiens

<400> SEQUENCE: 3

Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Val Leu Thr
            20                  25                  30

Lys Asp Gly Arg Ser Asn Val Arg Met Glu His Ile Ala Asp Lys Arg
        35                  40                  45

Phe Leu Tyr Leu Lys Asp Leu Trp Thr Thr Phe Ile Asp Met Gln Trp
    50                  55                  60

Arg Tyr Lys Leu Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Val Gln Val
            100                 105                 110

His Thr Leu Thr Gly Ala Phe Leu Phe Ser Leu Glu Ser Gln Thr Thr
        115                 120                 125

Ile Gly Tyr Gly Phe Arg Tyr Ile Ser Glu Glu Cys Pro Leu Ala Ile
    130                 135                 140

Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                165                 170                 175

Glu Thr Ile Arg Phe Ser Gln His Ala Val Val Ala Ser His Asn Gly
            180                 185                 190
```

```
Lys Pro Cys Leu Met Ile Arg Val Ala Asn Met Arg Lys Ser Leu Leu
            195                 200                 205

Ile Gly Cys Gln Val Thr Gly Lys Leu Leu Gln Thr His Gln Thr Lys
    210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255

His Val Val Asp Glu Thr Ser Pro Leu Lys Asp Leu Pro Leu Arg Ser
                260                 265                 270

Gly Glu Gly Asp Phe Glu Leu Val Leu Ile Leu Ser Gly Thr Val Glu
            275                 280                 285

Ser Thr Ser Ala Thr Cys Gln Val Arg Thr Ser Tyr Leu Pro Glu Glu
    290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
                325                 330                 335

Ala Ser Pro Ser Gly Leu Arg Asp Ser Thr Val Arg Tyr Gly Asp Pro
            340                 345                 350

Glu Lys Leu Lys Leu Glu Glu Ser Leu Arg Glu Gln Ala Glu Lys Glu
    355                 360                 365

Gly Ser Ala Leu Ser Val Arg Ile Ser Asn Val
            370                 375

<210> SEQ ID NO 4
<211> LENGTH: 25
<212> TYPE: PRT
<213> ORGANISM: homo sapiens

<400> SEQUENCE: 4

Ala Val Ala His Gly Asp Leu Leu Glu Leu Asp Pro Pro Ala Asn His
1               5                   10                  15

Thr Pro Cys Val Val Gln Val His Thr
            20                  25

<210> SEQ ID NO 5
<211> LENGTH: 9
<212> TYPE: PRT
<213> ORGANISM: homo sapiens

<400> SEQUENCE: 5

Arg Tyr Ile Ser Glu Glu Cys Pro Leu
1               5

<210> SEQ ID NO 6
<211> LENGTH: 27
<212> TYPE: DNA
<213> ORGANISM: artificial sequence
<220> FEATURE:
<223> OTHER INFORMATION: /note="Description of artificial sequence:
      primer"

<400> SEQUENCE: 6
ggatccatga cgtcagttgc caaggtg                                          27

<210> SEQ ID NO 7
<211> LENGTH: 27
<212> TYPE: DNA
<213> ORGANISM: artificial sequence
```

-continued

```
<220> FEATURE:
<223> OTHER INFORMATION: /note="Description of artificial sequence:
      primer"

<400> SEQUENCE: 7
ctcgagtcag acattgctga tgcgcac                                           27

<210> SEQ ID NO 8
<211> LENGTH: 44
<212> TYPE: DNA
<213> ORGANISM: artificial sequence
<220> FEATURE:
<223> OTHER INFORMATION: /note="Description of artificial sequence:
      primer"

<400> SEQUENCE: 8
gcggccgcac catgacgtca gttgccaagg tgtattacag tcag                        44

<210> SEQ ID NO 9
<211> LENGTH: 45
<212> TYPE: DNA
<213> ORGANISM: artificial sequence
<220> FEATURE:
<223> OTHER INFORMATION: /note="Description of artificial sequence:
      primer"

<400> SEQUENCE: 9
ctcgagtcag tggtggtggt ggtggtggac attgctgatg cgcac                       45
```